US008609639B2

(12) United States Patent
Turkson et al.

(10) Patent No.: US 8,609,639 B2
(45) Date of Patent: Dec. 17, 2013

(54) STAT3 INHIBITOR HAVING ANTI-CANCER ACTIVITY AND METHODS

(75) Inventors: James Turkson, Orlando, FL (US); Said Sebti, Tampa, FL (US); Richard Jove, Glendora, CA (US); Andrew D. Hamilton, Oxford (GB)

(73) Assignees: University of South Florida, Tampa, FL (US); Yale University, New Haven, CT (US); University of Central Florida Research Foundation, Inc., Orlando, FL (US)

( * ) Notice: Subject to any disclaimer, the term of this patent is extended or adjusted under 35 U.S.C. 154(b) by 466 days.

(21) Appl. No.: 12/517,453

(22) PCT Filed: Dec. 5, 2007

(86) PCT No.: PCT/US2007/086453
§ 371 (c)(1),
(2), (4) Date: Jan. 19, 2011

(87) PCT Pub. No.: WO2008/070697
PCT Pub. Date: Jun. 12, 2008

(65) Prior Publication Data
US 2011/0124602 A1 May 26, 2011

Related U.S. Application Data

(60) Provisional application No. 60/868,794, filed on Dec. 6, 2006.

(51) Int. Cl.
*A61K 31/675* (2006.01)
*C07F 9/653* (2006.01)
*C12N 5/071* (2010.01)

(52) U.S. Cl.
USPC .............. 514/92; 435/366; 435/375; 548/119

(58) Field of Classification Search
None
See application file for complete search history.

(56) References Cited

U.S. PATENT DOCUMENTS

2008/0045528 A1* 2/2008 Sutton et al. ............... 514/233.8

FOREIGN PATENT DOCUMENTS

| | | |
|---|---|---|
| AT | 07868993.2 | 12/2007 |
| BE | 07868993.2 | 12/2007 |
| BG | 07868993.2 | 12/2007 |
| CA | 2671121 | 12/2007 |
| CH | 07868993.2 | 12/2007 |
| CY | 07868993.2 | 12/2007 |
| CZ | 07868993.2 | 12/2007 |
| DE | 07868993.2 | 12/2007 |
| DK | 07868993.2 | 12/2007 |
| EE | 07868993.2 | 12/2007 |
| EP | 07868993.2 | 12/2007 |
| ES | 07868993.2 | 12/2007 |
| FI | 07868993.2 | 12/2007 |
| FR | 07868993.2 | 12/2007 |
| GB | 07868993.2 | 12/2007 |
| GR | 07868993.2 | 12/2007 |
| HU | 07868993.2 | 12/2007 |
| IE | 07868993.2 | 12/2007 |
| IS | 07868993.2 | 12/2007 |
| IT | 07868993.2 | 12/2007 |
| LT | 07868993.2 | 12/2007 |
| LU | 07868993.2 | 12/2007 |
| LV | 07868993.2 | 12/2007 |
| MC | 07868993.2 | 12/2007 |
| MT | 07868993.2 | 12/2007 |
| NL | 07868993.2 | 12/2007 |
| PL | 07868993.2 | 12/2007 |
| PT | 07868993.2 | 12/2007 |
| RO | 07868993.2 | 12/2007 |
| SE | 07868993.2 | 12/2007 |
| SI | 07868993.2 | 12/2007 |
| SK | 07868993.2 | 12/2007 |
| TR | 07868993.2 | 12/2007 |
| WO | WO 2006/091837 | 8/2006 |
| WO | PCT/US07/086453 | 12/2007 |
| WO | WO 2008/070697 | 6/2008 |

OTHER PUBLICATIONS

U.S. Appl. No. 60/868,794, filed Dec. 6, 2006, James Turkson.
Becker S, et al. (1998) Three-dimensional structure of the Stat3beta homodimer bound to DNA. Nature. 394: 145-151.
Bence NF, et al. (2001) Impairment of the ubiquitin-proteasome system by protein aggregation. Science. 29: 1552-1555.
Bennett EJ, et al. (2005) Global impairment of the ubiquitin-proteasome system by nuclear or cytoplasmic protein aggregates precedes inclusion body formation. Mol Cell. 17: 351-365.
Bowman T, et al. (2000) Stat3-mediated Myc expression is required for Src transformation and PDGF-induced mitogenesis. Proc Natl Acad Sci USA. 98: 7319-7324.
Bowman T, et al. (2000) STATs in oncogenesis. Oncogene. 19: 2474-2488.
Bromberg JF, et al. (1998) Stat3 activation is required for cellular transformation by v-src. Mol Cell Biol. 18: 2553-2558.
Buettner R, et al. (2002) Activated STAT signaling in human tumors provides novel molecular targets for therapeutic intervention. Clin Cancer Res. 8: 945-954.
Catlett-Falcone R, et al. (1999) Constitutive activation of Stat3 signaling confers resistance to apoptosis in human U266 myeloma cells. Immunity. 10: 105-115.
Ciechanover A, et al. (2000) Ubiquitin-mediated proteolysis: biological regulation via destruction. Bioassays. 22: 442-451.

(Continued)

*Primary Examiner* — Kamal Saeed
(74) *Attorney, Agent, or Firm* — Ballard Spahr LLP

(57) ABSTRACT

A small-molecule Stat3 dimerization inhibitor, S3I-M2001, is described and the dynamics of intracellular processing of activated Stat3 within the context of the biochemical and biological effects of the Stat3 chemical probe inhibitor are elucidated. S3I-M2001 is a newly-identified oxazole-based peptidomimetic of the Stat3 Src Homology (SH) 2 domain-binding phosphotyrosine peptide that selectively disrupts active Stat3:Stat3 dimers. Stat3-dependent malignant transformation, survival, and migration and invasion of mouse and human cancer cells harboring persistently-activated Stat3 were inhibited by S3I-M2001. S3I-M2001 inhibited Stat3-dependent transcriptional regulation of tumor survival genes, such as Bcl-xL. The disclosed compound is useful as a new potential treatment for certain cancers.

21 Claims, 12 Drawing Sheets

(56) References Cited

OTHER PUBLICATIONS

Darnell JE, Jr. (1996) The JAK-STAT pathway: summary of initial studies and recent advances. Recent Prog Horm Res. 51: 391-403.
Darnell JE, Jr. (1997) STATs and gene regulation. Science. 277: 1630-1635.
Darnell JE. (2005) Validating Stat3 in cancer therapy. Nat Med. 11: 595-596.
Garcia R, et al. (1997) Constitutive activation of Stat3 in fibroblasts transformed by diverse oncoproteins and in breast carcinoma cells. Cell Growth Differ. 8: 1267-1276.
Garcia R, et al. (2001) Constitutive activation of Stat3 by the Src and JAK tyrosine kinases participates in growth regulation of human breast carcinoma cells. Oncogene. 20: 2499-2513.
Garcia-Mata R, et al. (1999) Characterization and dynamics of aggresome formation by a cytosolic GFP-chimera. J Cell Biol. 146: 1239-1254.
Gelman MS, et al. (2002) a principal role for the proteasome in endoplasmic reticulum-associated degradation of misfolded intracellular cystic fibrosis transmembrane conductance regulator. J Cell Biol. 277: 11709-11714.
Gouillex F, et al. (1995) Prolactin and interleukin-2 receptors in T lymphocytes signal through MGF-STAT5-like transcription factor. Endocrinology. 136: 5700-5708.
Haura EB, et al. (2005) Mechanisms of disease: Insights into the emerging role of signal transducers and activators of transcription in cancer. Nat Clin Pract Oncol. 2: 315-324.
Huang et al. (2006) Inhibition of Stat3 activity with AG490 decreases the invasion of human pancreatic cancer cells in vitro. Cancer Sci. 97 1417-1423.
Herrmann A, et al. (2004) STAT3 is enriched in nuclear bodies. J Cell Sci. 117: 339-349.
Jing N, et al. (2003) Targeting Stat3 with G-quartet oligodeoxynucleotides in human cancer cells. DNA Cell Biol. 22: 685-696.
Johnston JS, et al. (1998) Aggresomes: a cellular response to misfolded proteins. J Cell Biol. 143: 1883-1898.
Jones G, et al. (1997) Development and validation of a genetic algorithm for flexible docking. J Mol Biol. 267: 727-748.
Kuriyan J, et al. (1997) Modular peptide recognition domains in eukaryotic signaling. Annu Rev Biophys Biomol Struct. 26: 259-288.
Lee TR, et al. (2000) SH2-directed ligands of the Lck tyrosine kinase. J Med Chem. 43: 1173-1179.
Nagel-Wolfrum K, et al. (2004) The interaction of specific peptide aptamers with the DNA binding domain and the dimerization domain of the transcription factor Stat3 inhibits transactivation and induces apoptosis in tumor cells. Mol Cancer Res. 2: 170-182.
Nam S, et al. (2005) Indirubin derivatives inhibit Stat3 signaling and induced apoptosis in human cancer cells. Proc Natl Acad Sci USA. 102: 5998-6003.
Niu G, et al. (2002) Constitutive Stat3 activity up-regulates VEGF expression and tumor angiogenesis. Oncogene. 21: 2000-2008.
Scholz Ash, et al. (2003) Activated signal transducer and activator of transcription 3 (STAT3) supports the malignant phenotype of human pancreatic cancer. Gastroenterology. 125: 891-905.
Seidel HM, et al. (1995) Spacing of palindromic half sites as a determinant of selective STAT (signal transducers and activators of transcription) DNA binding and transcriptional activity. Proc Natl Acad Sci USA. 92: 3041-3045.
Shuai K, et al. (1993) a single phosphotyrosine residue of Stat91 required for gene activation by interferon-gamma. Science. 261: 1744-1746.
Shuai K, et al. (1994) Interferon activation of the transcription factor Stat91 involves dimerization through SH2-phosphotyrosyl peptide interactions. Cell. 76: 821-828.
Siddiquee K et al. (2007) Selective chemical probe inhibitor of Stat3, identified through structure-based virtual screening induces antitumor activity. Proc Nat'l. Acad. Sci. USA. 104: 7391-7396.
Song H, et al. (2005) A low-molecular-weight compound discovered through virtual database screening inhibits Stat3 function in breast cancer cells. Proc Natl Acad Sci USA. 102: 4700-4705.
Szebenyi G, et al. (2007) Hook2 contributes to aggresome formation. BMC Cell Biol. 8: 19.
Turkson J, et al (2005) A novel platinum compound inhibits constitutive Stat3 signaling and induces cell cycle arrest and apoptosis of malignant cells. J Biol Chem. 280: 32979-32988.
Turkson J, et al. (1998) Stat3 activation by Src induces specific gene regulation and is required for cell transformation. Mol Cell Biol. 18: 2545-2552.
Turkson J, et al. (1999) Requirement for Ras/Rac 1 -mediated p38 and c-Jun N-terminal kinase signaling in Stat3 transcriptional activity induced by the Src oncoprotein. Mol Cell Biol. 19: 7519-7528.
Turkson J, et al. (2001) Phosphotyrosyl peptides block Stat3-mediated DNA binding activity, gene regulation, and cell transformation. J Biol Chem. 276: 45443-45455.
Turkson J, et al. (2004) Novel peptidomimetic inhibitors of signal transducer and activator of transcription 3 dimerization and biological activity. Mol Cancer Ther. 3: 261-269.
Turkson J, et al. (2004) Inhibition of constitutive signal transducer and activator of transcription 3 activation by novel platinum complexes with potent antitumor activity. Mol Cancer Ther. 3: 1533-1542.
Turkson J. (2004) STAT proteins as novel targets for cancer drug discovery. Expert Opin Ther Targets. 8: 409-422.
Turkson J. et al. (2000) STAT proteins: novel molecular targets for cancer drug discovery. Oncogene. 19: 6613-6626.
Wagner BJ, et al. (1990) The SIF binding element confers sis/PDGF inducibility onto the c-fos promoter. EMBO J. 9: 4477-4484.
Wipf P, et al. (1993) Stereospecific synthesis of peptide analogs with allo-threonine and D-allo-threonine residues. J Org Chem. 58: 3604-3606.
Xie K, et al. (2006) Transcriptional anti-angiogenesis therapy of human pancreatic cancer. Cytokine Growth Factor Rev. 17: 147-156.
Xie TX, et al. (2004) Stat3 activation regulates the expression of matrix metalloproteinase-2 and tumor invasion and metastasis. Oncogene. 23: 3550-3560.
Yu C, et al. (1995) Enhanced DNA-binding activity of a Stat3-related protein in cells transformed by the Src oncoprotein. Science. 269: 81-83.
Yu H, et al. (2004) The STATs of cancer—new molecular targets come of age. Nat Rev Cancer. 4: 97-105.
Zhang Y, et al. (2000) Activation of Stat3 in v-Src-transformed fibroblasts requires cooperation of Jak1 kinase activity. J Biol Chem. 275: 24935-24944.
Request for Reinstatement filed Jul. 4, 2013 for Canadian Patent Application No. 2671121, which claims priority to PCT Application No. PCT/US2007/086453 filed on Dec. 5, 2007 (Applicants—University of Central Florida Research Foundation, et al. // Inventors—James Turkson et al.) (1 Page).
International Search Report issued on Aug. 18, 2008 for PCT Application No. PCT/US2007/086453 filed on Dec. 5, 2007, which published as WO 2008/070697 on Jun. 12, 2008 (Applicants—University of Central Florida Research Foundation, et al. // Inventors—James Turkson et al.) (2 Pages).
Written Opinion issued on Aug. 18, 2008 for PCT Application No. PCT/US2007/086453 filed on Dec. 5, 2007, which published as WO 2008/070697 on Jun. 12, 2008 (Applicants—University of Central Florida Research Foundation, et al. // Inventors—James Turkson et al.) (4 Pages).
International Preliminary Report on Patentability issued on Jun. 10, 2009 for PCT Application No. PCT/US2007/086453 filed on Dec. 5, 2007, which published as WO 2008/070697 on Jun. 12, 2008 (Applicants—University of Central Florida Research Foundation, et al. // Inventors—James Turkson et al.) (5 Pages).
Communication conveying extended European Search Report issued Oct. 10, 2011 for EP Application No. 07868993.2, which claims priority to PCT/US2007/086453 filed on Dec. 5, 2007 (Applicants—University of Central Florida Research Foundation, et al.// Inventors—James Turkson et al.) (5 Pages).
Response to Extended European Search Report filed Apr. 16, 2012 for European Patent Application No. 07868993.2, which claims priority to PCT/US2007/086453 filed on Dec. 5, 2007 (Applicants—University of Central Florida Research Foundation, et al. // Inventors—James Turkson et al.) (10 Pages).

(56) References Cited

OTHER PUBLICATIONS

Communication under Rule 71(3) EPC—Intention to Grant issued on Sep. 20, 2012 for European Patent Application No. 07868993.2, which claims priority to PCT/US2007/086453 filed on Dec. 5, 2007 (Applicants—University of Central Florida Research Foundation, et al. // Inventors—James Turkson et al.) (5 Pages).

Decision to grant a European patent pursuant to Article 97(1) EPC issued on Feb. 21, 2013 for European Patent Application No. 07868993.2, which claims priority to PCT/US2007/086453 filed on Dec. 5, 2007 (Applicants—University of Central Florida Research Foundation, et al. // Inventors—James Turkson et al.) (2 Pages).

Request for Correction of Applicant Rule 139 filed on Feb. 28, 2013 for European Patent Application No. 07868993.2, which claims priority to PCT/US2007/086453 filed on Dec. 5, 2007 (Applicants—University of Central Florida Research Foundation, et al. // Inventors—James Turkson et al.) (14 Pages).

Request for Correction of Applicant Rule 139 filed on Mar. 8, 2013 for European Patent Application No. 07868993.2, which claims priority to PCT/US2007/086453 filed on Dec. 5, 2007 (Applicants—University of Central Florida Research Foundation, et al. // Inventors—James Turkson et al.) (2 Pages).

Refusal of request for correction after grant issued on Mar. 11, 2013 for European Patent Application No. 07868993.2, which claims priority to PCT/US2007/086453 filed on Dec. 5, 2007 (Applicants—University of Central Florida Research Foundation, et al. // Inventors—James Turkson et al.) (1 Page).

Communication of corrected entries under Rule 139 EPC issued on Mar. 21, 2013 for European Patent Application No. 07868993.2, which claims priority to PCT/US2007/086453 filed on Dec. 5, 2007 (Applicants—University of Central Florida Research Foundation, et al. // Inventors—James Turkson et al.) (1 Page).

\* cited by examiner

A) Luciferase assay

| v-Src (4 µg) | - | + | + | + | | - | + | + | + |
| S3I-201 (µM) | 0 | 0 | 30 | 0 | | 0 | 0 | 30 | 0 |
| Stat3β (4 µg) | - | - | - | + | | - | - | - | + |

B) EMSA analysis

C) Lck-SH2 domain-peptide binding assay

| pTyr-peptide | - | + | - | + | + | + |
| Lck-SH2-GST | - | - | + | + | + | + |
| S3I-M2001 (µM) | - | - | - | - | 30 | 100 |

D) Analysis of Stat3 nuclear localization

STAT3 INHIBITOR HAVING ANTI-CANCER ACTIVITY AND METHODS

CROSS-REFERENCE TO RELATED APPLICATIONS

The present application is a national phase application of International Application No. PCT/US2007/086453 filed on Dec. 5, 2007, which claims priority to U.S. Provisional Patent Application No. 60/868,794 filed on Dec. 6, 2006, each of which is incorporated by reference herein it its entirety.

STATEMENT OF GOVERNMENT INTEREST

This invention was made with support from the U.S. Government under Grant CA 106439 awarded to James Turkson by the National Cancer Institute. Accordingly, the government has certain rights in the invention.

FIELD OF THE INVENTION

The present invention relates to the field of cellular biology and, more particularly, to a novel inhibitor effective against at least one protein of a certain family of proteins of importance in cancer cell physiology and known as Signal Transducers and Activators of Transcription (STAT).

BACKGROUND OF THE INVENTION

STAT proteins were originally discovered as latent cytoplasmic transcription factors that mediate cytokine and growth factor responses (1, 2). Seven members of the family, Stat1. Stat2. Stat3. Stat4. Stat5a and Stat5b, and Stat6, mediate several physiological effects including growth and differentiation, survival, development and inflammation. STATs are SH2 domain-containing proteins. Upon ligand binding to cytokine or growth factor receptors. STATs become phosphorylated on critical Tyr residue (Tyr705 for Stat3) by growth factor receptors, cytoplasmic Janus kinases (Jaks) or Src family kinases. Two phosphorylated and activated STAT monomers dimerize through reciprocal pTyr-SH2 domain interactions, translocate to the nucleus, and bind to specific DNA-response elements of target genes, thereby inducing gene transcription (1, 2). In contrast to normal STAT signaling, many human solid and hematological tumors harbor aberrant Stat3 activity (3-8 for reviews).

Constitutive Stat3 activity mediates dysregulated growth and survival, angiogenesis, as well as suppresses the host's immune surveillance of the tumor, making constitutively-active Stat3 a critical molecular mediator of carcinogenesis and tumor progression.

Genetic and other molecular evidence reveals persistent Tyr phosphorylation of Stat3 is mediated by aberrant upstream Tyr kinases and shows cancer cell requirement for constitutively-active and dimerized Stat3 for tumor maintenance and progression. Thus, in numerous proof-of-concept studies (9-13), inhibition of Stat3 activation or disruption of dimerization induces cancer cell death and tumor regression. How aberrant Stat3 is regulated for meeting the tumor-specific requirements in malignant cells remains undefined. There have been no studies into defining the molecular details of how malignant cells regulate aberrant Stat3 and how this regulation changes upon Stat3 inhibition prior to the onset of phenotypic changes, although knowing these events will facilitate efforts in modulating aberrant Stat3 for managing human cancers. Small-molecule Stat3 inhibitors thus provide tools for probing the molecular dynamics of the cellular processing of Stat3 to understand Stat3's role as a signaling intermediate and a molecular mediator of the events leading to carcinogenesis and malignant progression.

The computational analysis of the interaction between the Stat3 SH2 domain-binding pTyr peptide sequence and the SH2 domain, per the X-ray crystal structure of Stat3b bound to DNA (14), can generate valuable information about key structural requirements for the Stat3:Stat3 dimer formation that will facilitate the design of effective small-molecules to disrupt the dimer. Such molecules can be used for therapeutic purposes and as tools for investigating the regulation of Stat3 protein. In the molecular modeling of the Stat3 pTyr-SH2 domain interaction, the peptidomimetic inhibitor, ISS 610 (10) derived from the Stat3 SH2 domain-binding pTyr (Y*) peptide, PY*LKTK (9), was used as a chemical probe for interrogating the Stat3:Stat3 dimer interface in order to derive non-peptide mimics.

Herein, we describe the design and characterization of a novel oxazole-based peptidomimetic, designated S3I-M2001, as a selective disruptor of Stat3:Stat3 dimerization and inhibitor of Stat3 activation. We also describe our study of the stability and intracellular processing of aberrant Stat3 within the context of the activity of S3I-M2001 as a Stat3 inhibitor.

SUMMARY OF THE INVENTION

Signal Transducer and Activator of Transcription (Stat) 3 is hyperactivated in many human tumors and represents a valid target for small-molecule anticancer drug design. We present a novel small-molecule Stat3 dimerization inhibitor, S3I-M2001 and describe the dynamics of intracellular processing of activated Stat3 within the context of the biochemical and biological effects of the Stat3 chemical probe inhibitor. S3I-M2001 is a newly-identified oxazole-based peptidomimetic of the Stat3 Src Homology (SH) 2 domain-binding phosphotyrosine peptide that selectively disrupts active Stat3:Stat3 dimers. Consequently, hyperactivated Stat3, which hitherto occurs as "dot-like" structures of nuclear bodies, undergoes an early aggregation into non-functional perinuclear aggresomes and a late-phase proteasome-mediated degradation in malignant cells treated with S3I-M2001. Thus, S3I-M2001 inhibited Stat3-dependent transcriptional regulation of tumor survival genes, such as Bcl-xL. Furthermore. Stat3-dependent malignant transformation, survival, and migration and invasion of mouse and human cancer cells harboring persistently-activated Stat3 were inhibited by S3I-M2001. The ectopic expression of Stat3 SH2 domain rescued cells from S3I-M2001-induced apoptotic effects, further confirming a dimerization inhibition mechanism. Finally, S3I-M2001 inhibited growth of human breast tumor xenografts. The study identifies a novel Stat3 inhibitor, S3I-M2001 and provides evidence for antitumor cell effects mediated in part through a biphasic loss of functional Stat3. The disclosed study represents the first on intracellular Stat3 stability and processing following inhibition by a small-molecule that has significant antitumor activity.

With the foregoing in mind, the present invention advantageously provides a compound designated as S3I-M2001 and having a chemical structure according that shown in FIG. 1B, or a pharmaceutically acceptable salt thereof. The invention further includes a pharmaceutically acceptable composition containing the compound shown in FIG. 1B. In one preferred embodiment of the invention, a pharmaceutically acceptable composition contains the compound S3I-M2001 in an effective amount for inhibiting Stat3 dimerization upon contacting a mammalian cell.

Method aspects of the invention include treating a mammalian cell having a dysfunctional Stat3 protein, the method comprising contacting the cell with the compound S3I-M2001 or with a composition containing the compound. Treatment also includes inhibiting a mammalian cell harboring constitutively active Stat3 by contacting the cell with an effective amount of the compound S3I-M2001 or a composition containing the compound so as to inhibit the Stat3 activity in the cell. For example, in a method of treating human breast or pancreatic cancer characterized by a constitutively active level of Stat3, the method comprises administering a sufficient amount of the compound S3I-M2001, or a composition containing it, to contact cancer cells in the patient's breast or pancreas.

Alternatively, a patient may be treated to inhibit growth of a human breast cancer tumor by administering to the patient a sufficient amount of the compound of S3I-M2001 or a composition containing S3I-M2001. More broadly viewed, the invention includes a method of inhibiting migration of a malignant cell, the method comprising contacting the cell with S3I-M2001 as the compound or in a pharmaceutically acceptable composition.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

Figure 1:
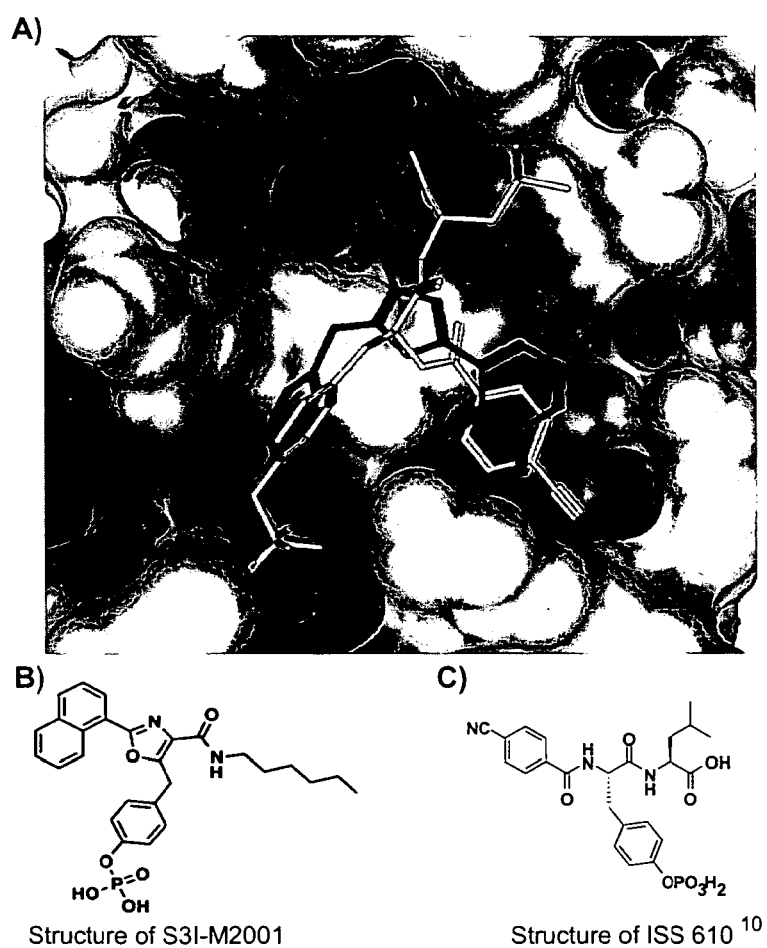
FIG. 1 shows computational modeling of S3I-M2001 bound to the Stat3 SH2 domain and S3I-M2001 chemical structure according to an embodiment of the present invention; in panel (A) S3I-M2001 (green) is shown docked to the SH2 domain of Stat3, along with Stat3 peptidomimetic inhibitor, ISS 610 (yellow) (10); and the chemical structures of S3I-M2001 (panel B) or ISS 610 (panel C) are shown.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Abbreviations used herein are as generally accepted and used by those skilled in the art and include the following: STAT, signal transducer and activator of transcription; PBS, phosphate-buffered saline; EMSA, electrophoretic mobility shift assay; FBS, fetal bovine serum; PMSF, phenylmethylsulfonylfluoride; and PNPP, p-nitrophenyl phosphate; YFP, yellow fluorescent protein; GFP, green fluorescent protein; CVFF, consistent valence forcefield; and CCDC, Cambridge Crystallographic Data Center.

Those skilled in the art will recognize that this invention encompasses pharmaceutical compositions and dosage forms containing the disclosed compound of the invention as an active ingredient. A "pharmaceutically acceptable composition" is compatible with the subject's physiology and may contain one or more pharmaceutically acceptable carriers or excipients. Some of these pharmaceutical compositions may be single unit dosage forms suitable for oral, topical, mucosal (e.g., nasal, pulmonary, sublingual, vaginal, buccal, or rectal), parenteral (e.g., subcutaneous, intravenous, bolus injection, intramuscular, or intraarterial), or transdermal administration to a patient. As known to the skilled, examples of dosage forms include, without limitation: tablets; caplets; capsules, such as soft elastic gelatin capsules; cachets; troches; lozenges; dispersions; suppositories; ointments; poultices; pastes; powders; dressings; creams; plasters; solutions; patches; aerosols such as nasal sprays or inhalers; gels; liquid dosage forms for oral or mucosal administration, including aqueous or non-aqueous liquid suspensions, oil-in-water emulsions, or water-in-oil liquid emulsions, solutions, and elixirs; liquid dosage forms suitable for parenteral administration to a patient; and sterile solids such as crystalline or amorphous solids that can be reconstituted to provide liquid dosage forms suitable for parenteral administration to a patient.

The skilled will also know that a formulation should suit the mode of administration. For example, oral administration may require an enteric coating to help protect the active ingredient from degradation in the gastrointestinal tract. The S3I-M2001 may also be administered in a liposomal formulation to shield it from enzymes that may degrade it, to facilitate transport in the blood and to aid in its delivery across cell membranes.

The composition of S3I-M2001, shape, and type of dosage forms of the invention will typically vary depending on the intended use. Thus, it would follow that in the acute treatment of a disease the dosage may contain larger amounts of the compound, whereas in the chronic treatment of the same disease a lower dosage may suffice. Likewise, smaller amounts of S3I-M2001 may be used in a parenteral dose than in an dose form used to treat the same disease. The ways in which specific dosage forms for the invention may be changed will be appreciated by the skilled, particularly with reference to a recognized treatise such as *Remington's Pharmaceutical Sciences,* 18th ed., Mack Publishing, Easton Pa. (1990).

As used herein, the term "Stat" refers to signal transducers and activators of transcription, which represent a family of proteins that, when activated by protein tyrosine kinases in the cytoplasm of the cell, migrate to the nucleus and activate gene transcription. Examples of mammalian STATs include STAT 1, STAT2, STAT3, STAT4, STAT5a, STAT5b, and STATE.

The term "pharmaceutically acceptable salt or prodrug" is intended to describe any form (such as an ester, phosphate ester, salt of an ester or a related group) of a compound of the invention, which, upon administration to a subject, provides the mature or base compound (e.g., the Stat3-inhibitory compound S3I-M2001). Pharmaceutically compatible salts include those derived from inorganic or organic bases and acids which are compatible with the subject's physiology. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The terms "signaling" and "signaling transduction" represent the biochemical process involving transmission of extracellular stimuli, via cell surface receptors through a specific and sequential series of molecules, to genes in the nucleus resulting in specific cellular responses to the stimuli.

"Constitutive activation" and "constitutively active," as in the constitutive activation of the STAT pathway, refers to a condition where there is an abnormally elevated level of tyrosine phosphorylated STAT3 within a given cell(s). e.g., cancer cells, as compared to a corresponding normal (e.g., non-cancer or non-transformed) cell. Constitutive activation of STAT3 has been exhibited in a large variety of malignancies, including, for example, breast carcinoma cell lines; primary breast tumor specimens; ovarian cancer cell lines and tumors: multiple myeloma tumor specimens; and blood malignancies, such as acute myelogenous leukemia, as described in published PCT international application WO 00/44774 (Jove. R. et al.), the disclosure of which is incorporated herein by reference in its entirety.

Methods for determining whether a human or non-human mammalian cell or subject has abnormally high levels of constitutively-activated Stat3 are known in the art and are described, for example, in U.S. patent publication 2004-0138189-A1 and PCT publication 02/078617 A, each of which are incorporated herein by reference in its entirety. Optionally, the methods of the invention further comprise identifying a patient suffering from a condition (e.g., cancer) associated with an abnormally elevated level of tyrosine phosphorylated STAT3, or determining whether the cancer cells can be characterized as having abnormally elevated levels of tyrosine phosphorylated Stat3.

As used herein, the terms "treat," "treating" or "treatment" refer to both therapeutic treatment and prophylactic or preventative measures, wherein the object is to prevent or slow down (lessen) an undesired physiological change or disorder, such as the development or spread of cancer or other proliferation disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with a compound of the invention may include reduction of undesirable cell proliferation, and/or induction of apoptosis and cytotoxicity. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the patient may be identified (e.g., diagnosed) as one suffering from the disease or condition (e.g. proliferation disorder) prior to administration of the Stat3 inhibitor of the invention.

As used herein, the term "(therapeutically) effective amount" refers to an amount of the compound of the invention or a composition containing the compound effective to treat a disease or disorder in a mammal or a mammalian cell. In the case of cancer or other proliferation disorder, the therapeutically effective amount of the agent may reduce (i.e., slow to some extent and preferably stop) unwanted cellular proliferation; reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; reduce Stat3 signaling in the target cells (such as by inhibiting the binding of DNA and Stat3), and/or relieve, to some extent, one or more of the symptoms associated with the cancer. To the extent the administered compound or composition prevents growth and/or kills existing cancer cells, it may be cytostatic and/or cytotoxic. For cancer therapy, efficacy can, for example, be measured by assessing the time to disease progression (TTP) and/or determining the response rate (RR).

The terms "inhibit" or "inhibitory amount" when referring to the compound of the invention indicate an amount which slows or stops growth or proliferation of a target cell, such as a tumor cell, either in vitro or in vivo, irrespective of the mechanism by which cell growth is inhibited (e.g., by cytostatic properties, cytotoxic properties, etc.).

The terms "cell" and "cells" are used interchangeably herein and are intended to include either a single cell or a plurality of cells, in vitro or in vivo, unless otherwise specified.

Figure 2:
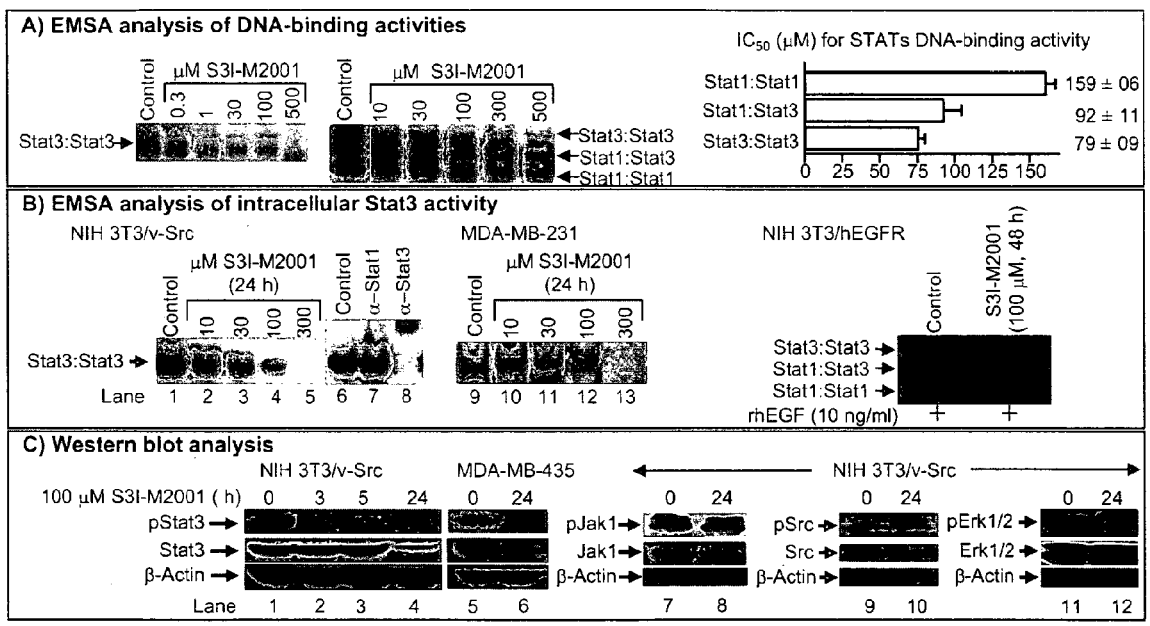
FIG. 2 depicts the effects of S3I-M2001 on STATs activation, and on pJak1, pSrc, pErk1/2; (A) shows EMSA analysis of STATs DNA-binding activities in nuclear extracts containing activated Stat3 (left panel) or Stat1 and Stat3 (middle panel) and pre-treated with S3I-M2001 concentrations for 30 min. at room temperature prior to incubation with radiolabeled hSIE oligonucleotide probe, and IC50 values for the inhibition of STATs DNA-binding activity in vitro (right panel) derived, as described in "Methods"; (B) EMSA analysis of Stat3 DNA-binding activity in nuclear extracts from NIH3T3/v-Src or MDA-MB-231 cells, or from recombinant human EGF (rhEGF)-stimulated NIH3T3/hEGFR mouse fibroblasts treated with or without S3I-M2001; and (C) SDS-PAGE/Western blot analysis of whole-cell lysates prepared from S3I-M2001-treated or untreated NIH3T3/v-Src or MDA-MB-435 cells probing for pTyr705Stat3, Stat3, pJak, Jak1, pSrc, Src, pErk1/2, Erk1/2, and b-actin; positions of STAT:DNA complex in gel, pTyrStat3 and Stat3 are labeled; values are the mean and S.D. of 3 replicate experiments: data are representative of three independent studies; IC50 values were determined by quantifying by ImageQuant the bands corresponding to the STAT:DNA complexes; control lanes represent nuclear extracts untreated with S3I-M2001 or nuclear extract preparations from cells untreated with the compound.
Figure 3:
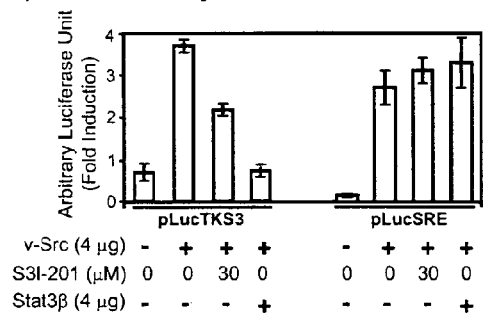
FIG. 3 illustrates the effects of S3I-M2001 on Stat3 transcriptional activity and dimerization, and nuclear localization, and on the Lck-SH2 domain function; in (A) are shown luciferase reporter measurements in cytosolic extracts prepared from NIH3T3 fibroblasts transiently co-transfected with the Stat3-dependent (pLucTKS3) or the Stat3-independent (pLucSRE) luciferase reporter together with the v-Src plasmid with and without Stat3b plasmid and treated with or without S3I-M2001; (B) shows EMSA analysis of STATs DNA-binding activities in independently-prepared cell lysates of activated Stat1 or Stat3, or mixed pool of lysates of both proteins and pre-treated with or without S3I-M2001 concentrations for 30 min at room temperature prior to incubation with radiolabeled hSIE oligonucleotide probe, as described in "Methods"; (C) depicts in vitro ELISA for the binding of Lck-SH2-GST to the conjugate biotinylated pTyr-peptide (EPQpYEEIEL) and effects of S3I-M2001; and (D) Immunofluorescence imaging/confocal microscopy of Stat3 nuclear localization in NIH3T3/hEGFR treated with or without 100 mM S3I-M2001 for 3 h prior to stimulation or unstimulation by EGF (rhEGF) for 10 min.: positions of STAT:DNA complex in gel are labeled; values are the mean and S.D. of 6 replicate experiments; data are representative of three independent studies.
Figure 3:
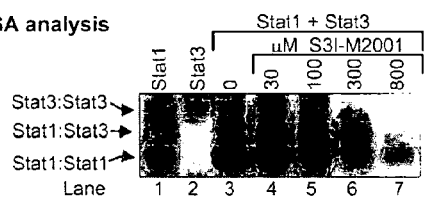
Figure 3:
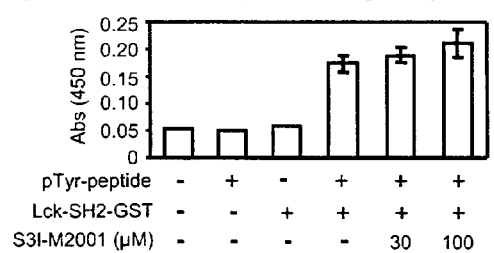
Figure 3:
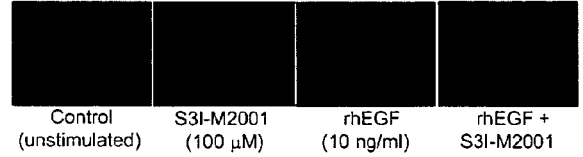
Figure 4:
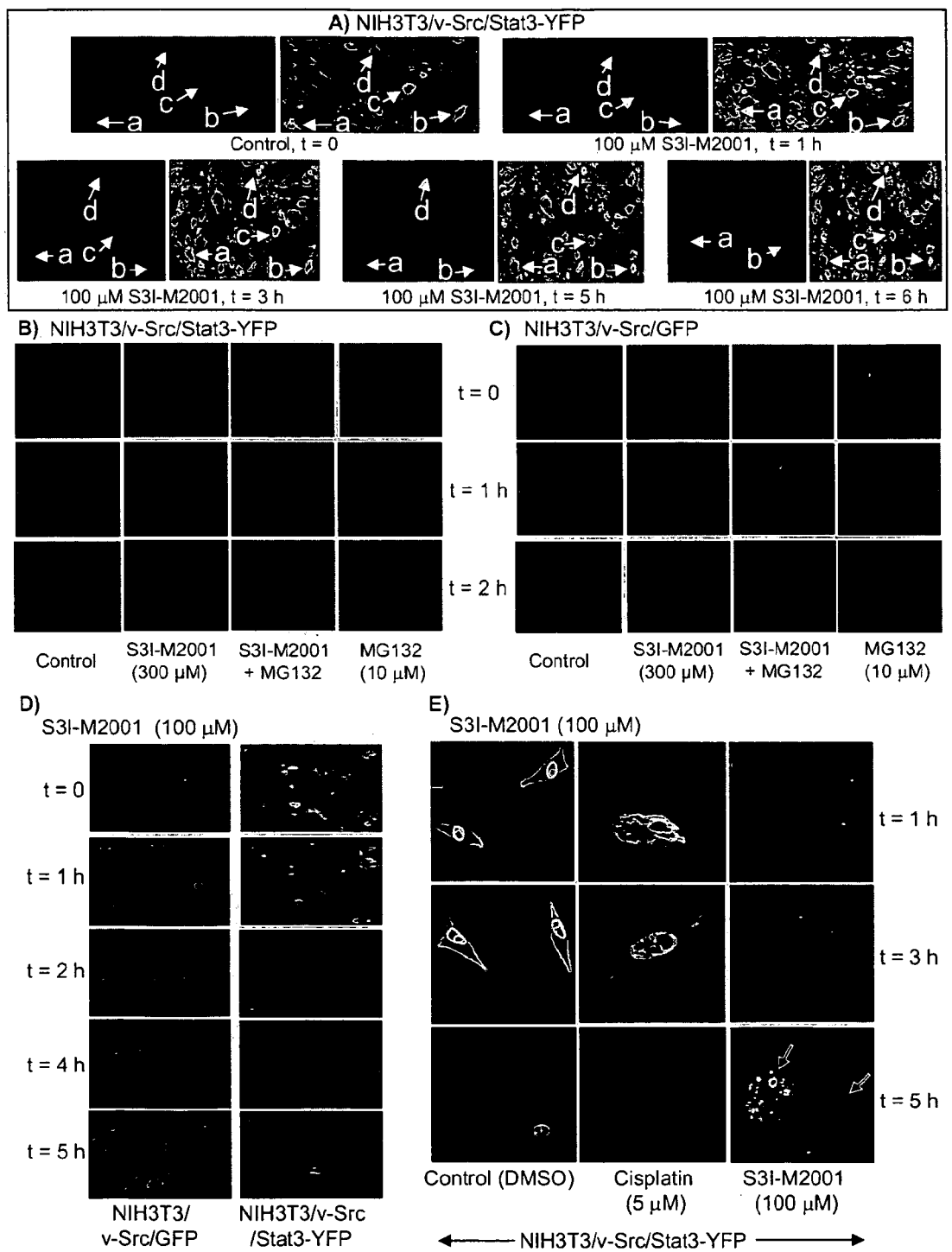
FIG. 4 shows fluorescence with confocal microscopy of intracellular Stat3 signal; fluorescence microscopy of the NIH3T3/v-Src fibroblasts stably expressing the plasmids for (A) and (B) yellow fluorescent protein (YFP)-tagged Stat3 (NIH3T3/v-Src/Stat3-YFP) or (C) green fluorescent protein (GFP) (NIH3T3/v-Src/GFP) and treated with or without S3I-M2001 for the indicated times in the presence or absence of the proteasome inhibitor, MG132 (1-h pre-treatment); and Laser scanning confocal microscopy of (D) NIH3T3/v-Src/GFP (left panel) or NIH3T3/v-Src/Stat3-YFP (right panel) or (E) NIH3T3/v-Src/Stat3-YFP and treated with or without S3I-M2001 or Cisplatin for the indicated times; fluorescence and confocal images were collected using Nikon Eclipse TE200 and Leica TCS SP5 microscopes, respectively; Arrows denote fluorescence or cells previously showing fluorescence, or aggregated Stat3-YFP; data are representative of 2-3 independent studies.
Figure 5:
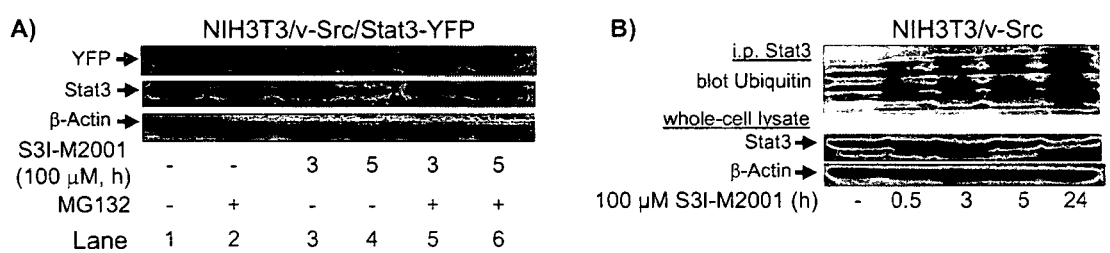
FIG. 5 displays immunoblotting analyses of intracellular Stat3 signal; SDS-PAGE/Western blot analysis of (A) whole-cell lysates from NIH3T3/v-Src/Stat3-YFP probing for YFP, Stat3 or b-actin; and (B) of Stat3 immunoprecipitates from NIH3T3/v-Src fibroblasts blotting for Ubiquitin, or NIH3T3/v-Src whole-cell lysates blotting for Stat3 or b-actin; data are representative of 2-3 independent studies.
Figure 6:
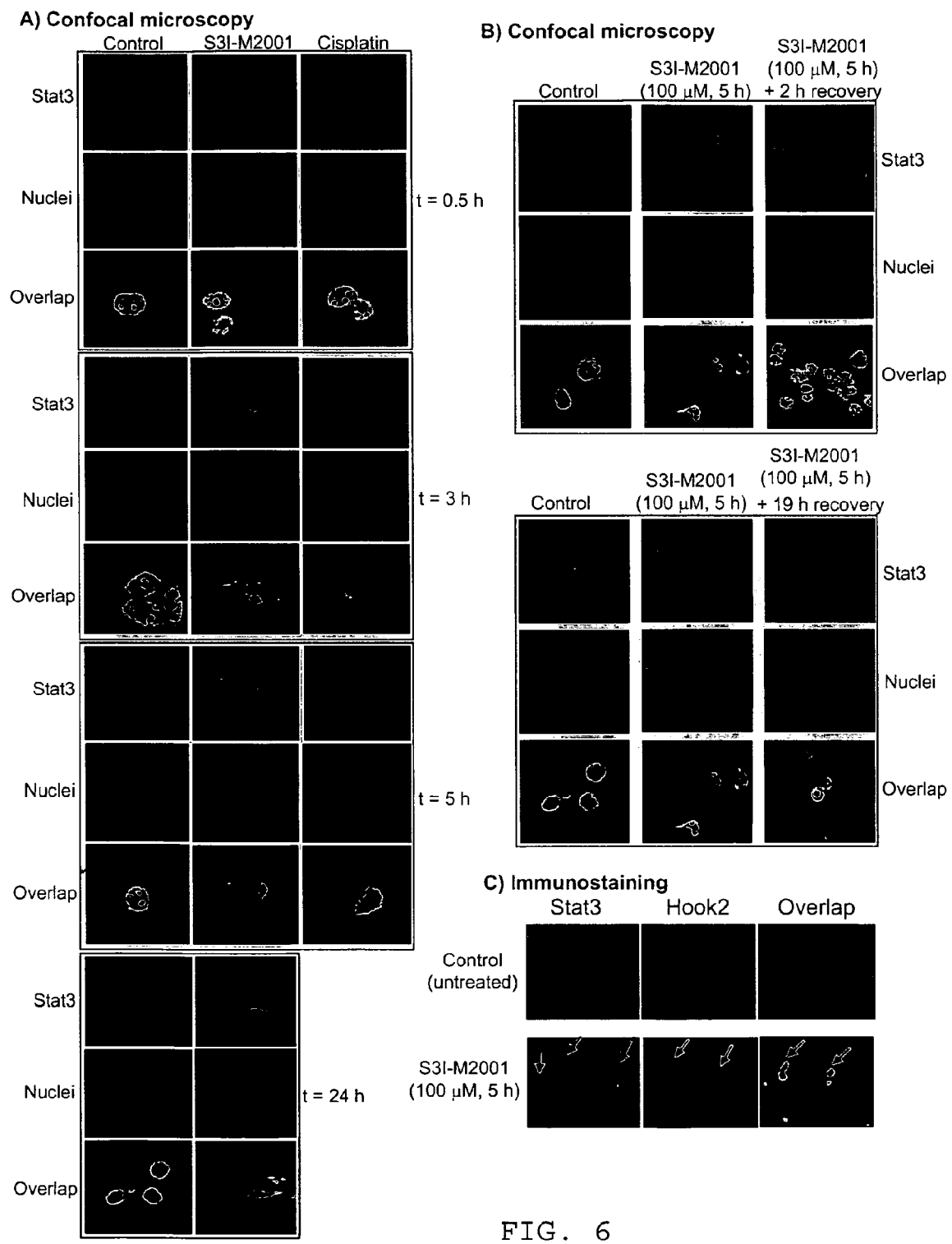
FIG. 6 shows immunofluorescence with laser scanning confocal imagining of Stat3 aggregation into perinuclear aggresomes induced by S3I-M2001: immunofluorescence and confocal microscopy of NIH3T3/v-Src fibroblasts growing in culture treated with or without S3I-M2001 or Cisplatin for the indicated times, (A) fixed and stained with rabbit anti-Stat3 antibody (green) or DAPI nuclear staining (blue); (B) allowed to recover from the effects of S3I-M2001 for 2 h or 19 h prior to fixing and staining for Stat3 or with DAPI; or (C) fixed and stained with rabbit antibody against Stat3 (green) or goat antibody against Hook2 (blue); arrows denote aggregated Stat3 and localization of Hook2 protein; images were captured using Leica TCS SP5 laser scanning confocal microscope and are representative of 3 independent experiments.
Figure 7:
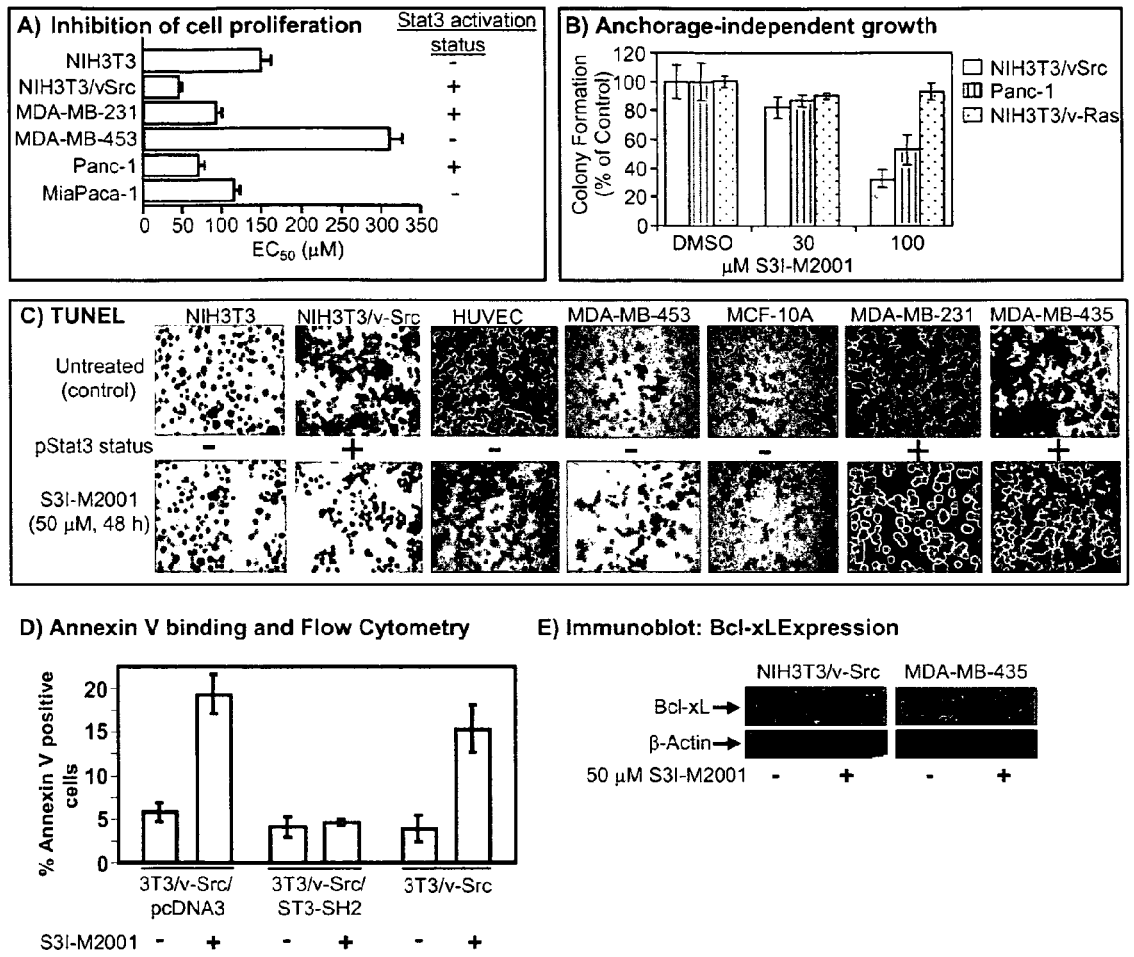
FIG. 7 shows effect of S3I-M2001 on cell viability, malignant transformation, apoptosis and Bcl-xL expression: in (A) IC50 values for the S3I-M2001-induced loss of cell viability determined by WST-1 assay; (B) anchorage-independent growth in soft-agar suspension of malignant cells (NIH3T3/v-Src. Panc-1 and NIH3T3/v-Ras) treated with or without S3I-M2001 every three days; (C) TUNEL staining for DNA damage in normal NIH3T3 and NIH3T3/v-Src, human endothelial (HUVEC), breast cancer cells (MDA-MB-453, MDA-MB-231 and MDA-MB-435), and the normal breast epithelial MCF-10A cells treated with or without S3I-M2001 for 48 h; Stat3 activity status is indicated as (+), pStat3 (activated), (−), no Stat3 activity; (D) Annexin V binding and Flow Cytometry of NIH3T3/v-Src fibroblasts transfected with empty vector, pcDNA3 (3T3/v-Src/pcDNA3) or the Stat3 SH2 domain (3T3/v-Src/ST3-SH2) for 4 h or untransfected (3T3/v-Src) and treated with or without 100 mM S3I-M2001 for additional 24 h; and (E) SDS-PAGE and Western blot analysis for Bcl-xL in NIH3T3/v-Src and MDA-MB-435 cells; images shown are representative of 2-3 independent studies; values are the mean and S.D. of 3-4 replicate experiments.
Figure 8:
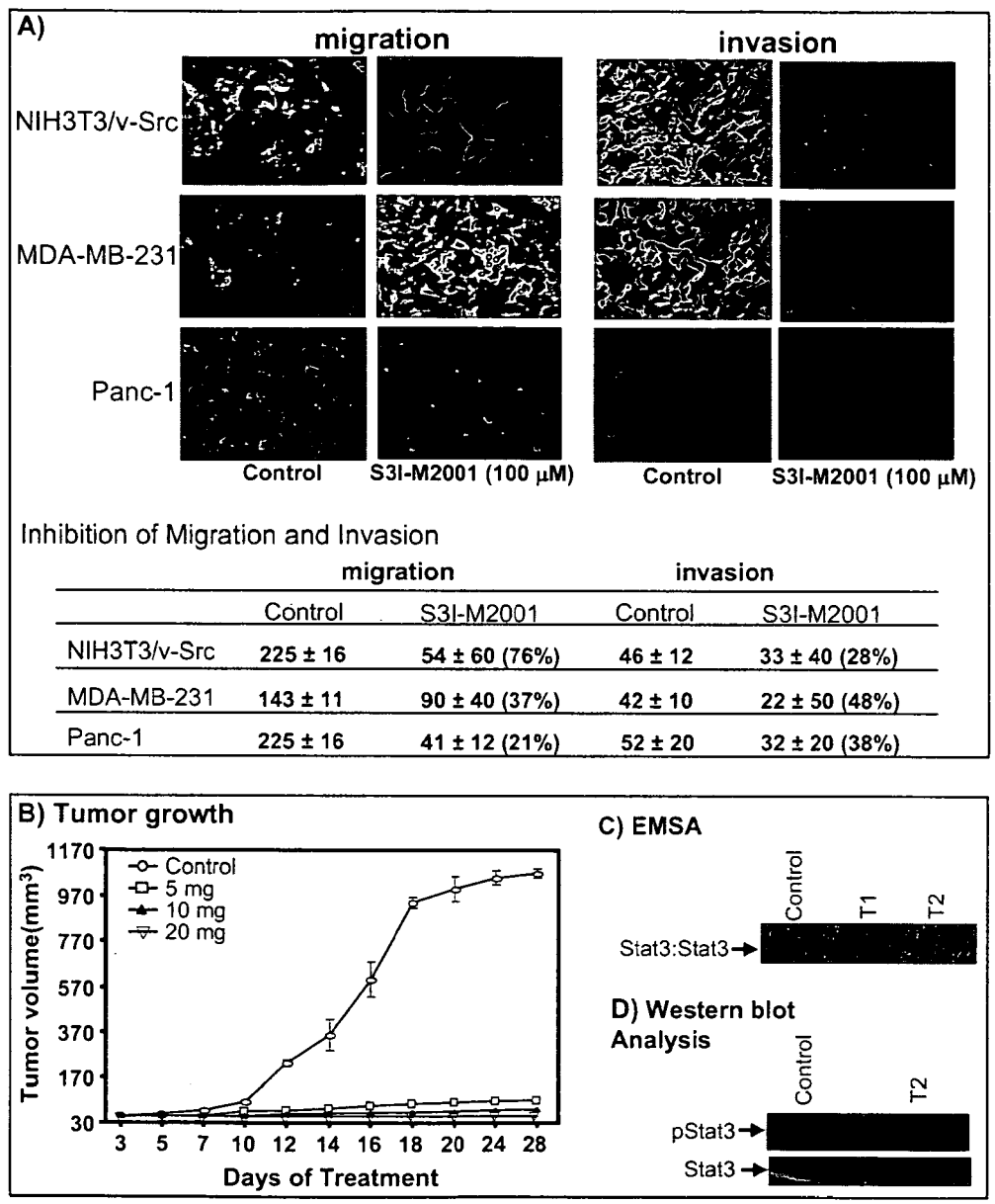
FIG. 8 shows that S3I-M2001 suppresses malignant cell migration and invasion and inhibits growth of human breast tumor xenografts; in (A) viral Src-transformed mouse fibroblasts (NIH3T3/v-Src), human breast cancer (MDA-MB-231) and pancreatic cancer (Panc-1) cells were seeded for studies in migration on filters or invasion on matrigel-coated filters in Bio-Coat chambers and treated with or without S3I-M2001 (100 mM) for 24; cells on other side of filters were photographed (upper panel) and quantified under light microscope (lower panel; percent inhibition in parenthesis): human breast (MDA-MB-231) tumor-bearing mice were given S3I-M2001 (5, 10 and 20 mg kg-1) i.v. every 2 or 3 days; (B) Tumor sizes, measured every 2 or 3 days, were converted to tumor volumes and plotted against treatment days; (C) EMSA analysis of Stat3 DNA-binding activity in lysates from tumor tissues extracted from one control and two residual treated tumors (T1 and T2) 3 days after the last S3I-M2001 (5 mg kg-1) injection; and (D) SDS-PAGE/Western blot analysis of whole-cell lysates from control or residual treated (T2) tumor tissue and probing for pTyr705Stat3 and Stat3; values are the mean and S.D. of three independent experiments each in duplicates or replicates of 12 tumor-bearing mice in each group; data are representative of 2-3 independent experiments; bands of Stat3:DNA complexes, pStat3 and Stat3 are shown.
Figure 9:
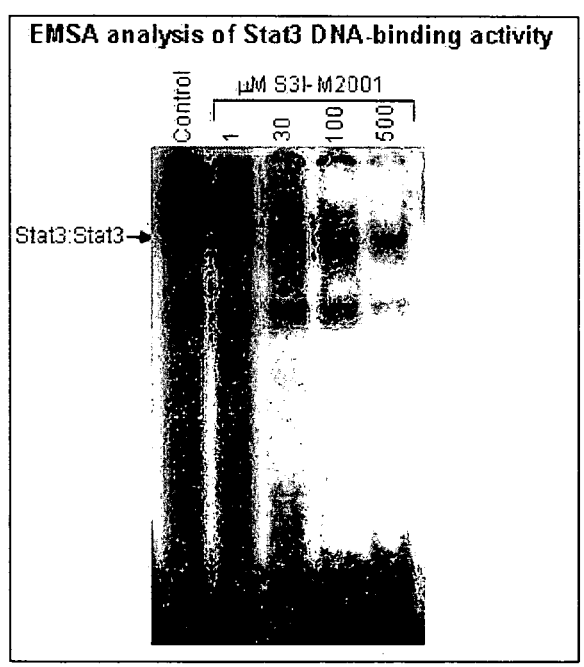
FIG. 9 shows effects of S3I-M2001 on STATs activation by EMSA analysis of Stat3 DNA-binding activity in cell lysate containing activated Stat3 prepared from Sf-9 cells infected with Stat3, Jak1, and c-Src baculoviruses: positions of STAT:DNA complex in gel are labeled; data shown are representative of 3 independent experiments.
Figure 10:
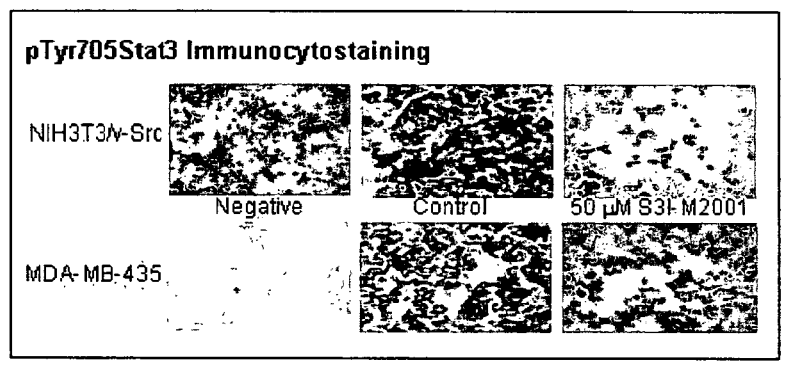
FIG. 10 depicts the effects of S3I-M2001 on Stat3 phosphorylation by immunohistochemical staining for pTyr705Stat3 in NIH3T3/v-Src or MDA-MB-435 cells; images are representative of three independent studies.
Figure 11:
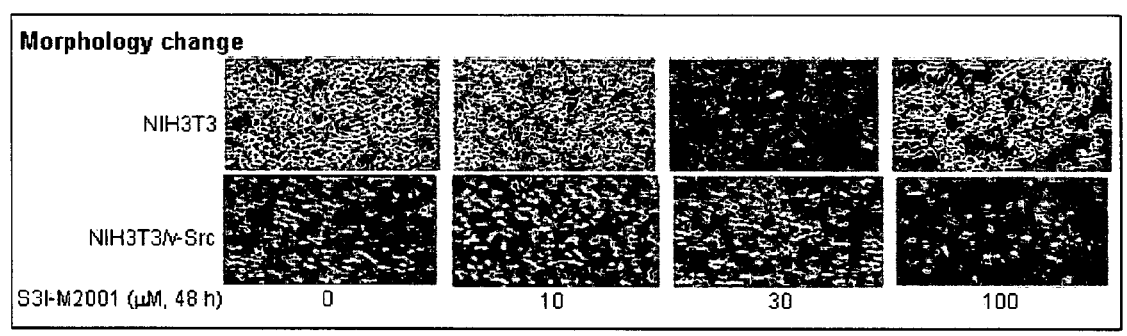
FIG. 11 illustrates the effect of S3I-M2001 on malignant transformation; images of cellular morphology are visualized using light microscope of normal NIH3T3 mouse fibroblasts and v-Src-transformed counterparts (NIH3T3/v-Src) growing in culture and treated with or without different concentrations of S3I-M2001 for 48 h; the images shown are representative of 2 independent studies.
Figure 12:
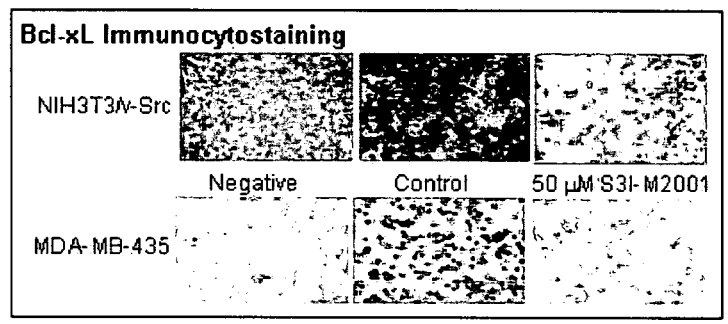
FIG. 12 shows the effect of S3I-M2001 on Bcl-xL expression by immunohistochemical staining for Bcl-xL in NIH3T3/v-Src and human breast cancer MDA-MB-435 cells; intense red staining indicates presence of Bcl-xL, while blue staining indicates absence of Bcl-xL; the images shown are representative of 3 independent studies.

FIGS. 1-8 visually present various aspects of the presently described invention and are more fully discussed below with reference to the results and conclusions derived from the investigation leading to the invention.

Methods

Cells and Reagents.

Normal mouse fibroblasts (NIH3T3) and counterparts transformed by v-Src transformed (NIH3T3/v-Src), v-Ras (NIH3T3/v-Ras), or overexpressing the human EGFR (NIH3T3/hEGFR), human breast cancer (MDA-MB-435, MDA-MB-453, MDA-MB-231 and MDA-MB-468), immortalized human breast epithelial cells. MCF-10A, and pancreatic cancer (Panc-1) cell lines have all been previously described (9-12, 17, 18, 40). Human umbilical vein cells (HUVEC) was a kind gift Dr. S. Chellappan of Moffitt Cancer Center and Research Institute (Tampa, Fla.). Cells were grown in Dulbecco's modified Eagle's medium (DMEM) containing 5% iron-supplemented bovine calf serum: MCF-10A were grown in DMEM:F12 media supplemented with 5% FBS, 10 mg mL-1 insulin, 500 ng mL-1 hydrocortisone, 20 ng mL-1 EGF, and 100 ng mL-1 cholera toxin. HUVEC cells were grown in Ham's F12k medium with 2 mM L-glutamine containing 1.5 g L-1 sodium bicarbonate and supplemented with 0.1 mg mL-1 heparin and 0.03 mg mL-1 endothelial cell growth supplement, and 10% FBS. WST-1 viability assay reagent was obtained from Roche and TUNEL assay kit was from BD Biosciences Pharmingen. Each treatment condition is a single dose at the indicated concentration or 0.1% DMSO (vehicle) as control. Anti-Hook2 antibody was from Santa Cruz. Plasmids. The pLucTKS3 and pLuc-SRE luciferase reporters have been previously reported (17, 19).

Computational Modeling of the Stat3 SH2 Domain-ISS 610 Complex.

As a first step towards designing new Stat3 inhibitors as probes or novel anticancer therapeutics, molecular modeling of the Stat3 SH2 domain was performed. The Stat3 SH2 domain contains trigonal arrangement of shallow pockets, deemed accessible by suitably-substituted heterocyclic scaffolds, such as the oxazole, S3I-M2001. Docking of S3I-M2001 into Stat3 was performed using the GOLD software (15) by CCDC. Compounds were drawn with Insight II (Accelrys), and energy minimized to a local minimum using the CVFF forcefield. The Stat3 protein was prepared for use in GOLD by adding Hydrogen atoms to the X-ray crystal structure, 1BG1.pdb (14. Compounds were docked by GOLD 10 times each using default settings within GOLD and were scored using the default GOLDScore scoring function. Maximum ligand flexibility was allowed during docking cycles by allowing ring flipping, amide cis/trans alteration, and amine flipping. After 10 dockings, the conformation with the highest score for each compound was considered and analyzed.

Compound Synthesis.

The design strategy for the construction of the oxazole scaffold was carried out using standard synthetic procedures, following the principle of rapid incorporation of structural diversity into an acyclic precursor, with subsequent late stage aromatization providing the desired heteroaryl array (41).

Recombinant Baculoviruses, Infection of Sf-9 Insect Cells and Cytosolic Lysates Preparation.

Infect of Sf-9 cells with Stat1, Stat3, Jak1, and c-Src recombinant baculoviruses and preparation of the cell lysates containing activated Stat1 or Stat3 have been previously described (9, 21).

Stat3 Inhibitory Property of S3I-M2001; Nuclear Extract Preparation and Gel Shift Assays.

In the previously reported dissociation-reassociation analysis (9, 10, 20), two independently-prepared cell lysate, one containing only activated Stat3:Stat3 dimer and the other containing only activated Stat1:Stat1 dimer (21), were mixed together and pre-treated with or without increasing concentration of S3I-M2001 and subjected to STAT DNA-binding assay with EMSA analysis.

Nuclear extract preparation from cells and EMSA were carried out as previously described (9-12, 16, 18, 40). Nuclear extract preparations from v-Src-transformed (NIH3T3/v-Src) or EGF-stimulated NIH3T3/hEGFR fibroblasts, or tumor cell lines were subjected to EMSA. The 32P-labeled oligonucleotide probe used was hSIE (high affinity sis-inducible element from the c-fos gene, m67 variant, as reported by Wagner et al. (42), and that binds Stat1 and Stat3. Except where indicated, inhibitor compound was pre-incubated with the nuclear extract for 30 min at room temperature prior to incubation with radiolabeled hSIE probe. Where necessary, cells were stimulated with recombinant human EGF (rhEGF) for 5-15 min prior to preparation of nuclear extracts. Bands corresponding to DNA-binding activities were scanned and quantified for each concentration of compound and plotted as percent of control (vehicle) against concentration of compound, from which the IC50 values were derived, as previously reported (9, 10, 42).

Immunoprecipitation (i.p.) and SDS-PAGE/Western Blot Analysis.

Whole-cell lysates prepared in boiling SDS sample-loading buffer. i.p. from lysates using monoclonal anti-Stat3 antibody (Cell Signaling Technology), and the probing of nitrocellulose membranes with primary antibodies and detection of horseradish peroxidase-conjugated secondary antibodies by enhanced chemiluminescence (Amersham Biosciences) were done, as previously described (13, 17, 19, 21). The probes used were anti-Stat3 (Santa Cruz), anti-pTyr705Stat3 (Cell Signaling Technology), anti-YFP antibodies (Santa Cruz), anti-Bcl-xL, anti-pSrc, anti-Src, anti-pJak1, anti-Jak1, anti-pEr1/2 and anti-Erk1/2, and b-actin (Cell Signaling Technology).

Dissociation-Reassociation Analysis.

The dissociation-reassociation analysis with EMSA analysis was performed, as previously done (10, 20).

Immunohistochemistry.

The indirect peroxidase-antiperoxidase test was performed on cytospins prepared from cell lines (control and treated with 50 mM S3I-M2001 for 48 h). Immunostaining was performed for pY705Stat3 with a rabbit anti-human polyclonal pYStat3 antibody (Cell Signaling Technology) and for Bcl-xL with rabbit monoclonal (E18) antibody (Abcam, Inc., Cambridge, Mass.) with rabbit immunoglobulins as negative controls using avidin-biotin-peroxidase complexes (Vector Laboratories, Burlingame, Calif.). After incubation and blocking of endogenous peroxidase and nonspecific background staining in 3% hydrogen peroxide and methanol for 20 min, slides were washed with PBS, treated with 1.5% normal serum and 3% BSA, and incubated with the pY705Stat3 or Bcl-xL primary antibodies overnight at 4° C. Slides were rinsed in PBS and incubated with a biotinylated secondary antibody (Vector Laboratories) for 60 min, followed by incubation with avidin-biotin-peroxidase complex for 1 h at room temperature. Chromagen was developed with Nova-Red. All slides were counterstained with hematoxylin for 30 s before dehydration and mounting. PhosphoY705Stat3 or Bcl-xL positive cells were stained red (due to Nova-Red) and negative cells were stained blue (due to hematoxylin).

Lck-SH2 Domain ELISA Assay.

An ELISA assay for the binding of Lck-SH2 domain with its conjugate phosphopeptide, biotinyl-e-Ac-EPQpYEEIEL-OH, was carried out, as previously described (13, 22). Absorbance reading (450 nm) for the peroxidase reaction was determined with an ELISA plate reader.

Fluorescence Microscopy.

NIH3T3/vSrc cells were either stably transfected with Stat3-YFP construct (23), or growing in 96-well plates on chamber slides were transiently transfected with the Stat3-YFP plasmid (23) using Lipofectamine 2000 for 24 h according to the manufacturer's protocol (Roche), treated with or without S3I-M2001 for different times, and examined under Nikon Eclipse TE200 fluorescence microscope (Nikon).

Images were captured and processed by NIKON NIS element-Basic research software.

Confocal Microscopy.

NIH3T3/hEGFR cells were grown in multi-cell plates and treated with or without S3I-M2001 for 3 h prior to stimulation by rhEGF (10 ng/ml) for 10 min or NIH3T3/vSrc cells were grown in multi-cell plates or chamber slides and cells were fixed with 4% paraformaldehyde for 15 min. Cells were washed 3 times in PBS, permeabilized with 0.2% Triton X for 5 min, and further washed 3-4 times with PBS. Specimens were then blocked in 5% goat serum for 60 min and incubated with Stat3 (Cell Signaling Technology) or Hook2 (Santa Cruz, Santa Cruz, Calif.) antibody at 1:50 dilution at 4° C. overnight. Subsequently, cells were rinsed 4-5 times in PBS, incubated with Alexa fluor 488 rabbit antibody (Molecular probe, Eugene, Oreg.) for (Stat3 detection) or NL637 goat antibody (R&D Systems, Minneapolis, Minn.) for Hook2 for 1-2 h at room temperature in the dark. Specimens were then washed 5 times with PBS, covered with cover slides with VECTASHIELD mounting medium containing DAPI, and examined immediately under Leica TCS SP5 confocal microscope (Germany) at appropriate wavelengths depending on GFP or YFP. Images were captured and processed using the Leica TCS SP 5 software.

Soft-Agar Colony Formation Assay.

Colony formation assays were carried out in six-well dishes and colonies were enumerated as previously described (19). Treatment with S3I-M2001 was initiated 1 day after seeding cells in soft-agar suspension by adding 75-100 mL of medium with or without compound, and repeated every three days, until large colonies were evident.

Cell Viability Assay, TUNEL Analysis, and Annexin V Binding and Flow Cytometry.

Normal NIH3T3 and NIH3T3/v-Src mouse fibroblasts growing in culture were treated with or without 10-100 mM S3I-M2001 for 48 h. Cells were then visualized under light microscope and photographed with a digital camera.

Proliferating cells in 96-well plates were treated with 50-300 mM S3I-M2001 for 48 h for WST-1 assay, according to manufacturer's (Roche) instructions, or cells growing in culture and treated with or without S3I-M2001 for 48 h were harvested for analysis by terminal nucleotidyl transferase mediated dUTP nick end labeling (TUNEL) staining according to supplier's (Roche) instructions to detect apoptotic cells. In some cases, cells were first transfected with the plasmid for the Stat3 SH2 (ST3-SH2) domain or mock-transfected (pcDNA3 empty vector) for 24 h or untransfected prior to treatment with S3I-M2001 for an additional 24-48 h. Cells were then detached and analyzed by Annexin V binding (BD Biosciences, San Diego) according to the manufacturer's protocol and Flow Cytometry to quantify the percent apoptosis.

Cell Migration and Matrigel Invasion Assays.

Cell migration experiments were carried out using Bio-Coat migration chambers (Becton Dickinson, Franklin, N.J.) of 24-well companion plates with cell culture inserts containing 8 mm pore size filters, according to the manufacturer's protocol. Briefly, tumor cells (5×104/500 ml) were added to each insert (upper chamber) with or without S3I-M2001 and medium with serum (10% FBS) as the chemoattractant was placed in each well of a 24-well companion plate (lower chamber). After 24-h incubation (37° C., 5% CO2), the filters were removed and the upper surface was wiped with a cotton-tipped applicator to remove non-migratory cells. Cells that had migrated through the filter pores and attached to bottom surface of the filter were fixed and stained. The membranes were mounted on glass slides and cells from 10 random microscopic fields (×400 magnification) were counted. Cell invasion experiments were performed using same Bio-Coat invasion chambers (Becton Dickenson), as already described, except that here, filters (8 mm) were used coated with the basement membrane matrigel. Percent inhibition is calculated as 100−y, where y equals residual number of stained cells in the treated/total number in the control ×100.

Mice and In Vivo Tumor Studies.

Six-week-old female athymic nude mice were purchased from Harlan and maintained in the institutional animal facilities approved by the American Association for Accreditation of Laboratory Animal Care. Athymic nude mice were injected subcutaneously in the left flank area with 5×106 human breast cancer MDA-MB-231 cells in 100 mL of PBS. After 5 to 10 days, tumors of a diameter of 3 mm were established. Animals were grouped so that the mean tumor sizes in all groups were nearly identical, given S3I-M2001 i.v. at 5, 10 and 20 mg/kg every 2 or every 3 days for 26 days and monitored every 2 or 3 days, and tumor sizes were measured with calipers. Tumor volume was calculated according to the formula $V=0.52 \times a2 \times b$, where a, smallest superficial diameter, b, largest superficial diameter.

Results and Discussion

Computational Modeling of the Stat3 SH2 Domain-ISS 610 Complex.

Close structural analysis of the lowest genetic optimization for ligand docking (GOLD) (15) conformation of ISS 610 (yellow) (IC50=42 μM for inhibition of Stat3:Stat3 (10)) bound within the Stat3 SH2 domain (FIG. 1A), per the X-ray crystal structure of Stat3b (14), indicated key structural requirements for hydrophobic, hydrogen-bonding, and electrostatic interactions critical for tight binding. Appropriate candidate binders are suitably-substituted heterocyclic systems that reproduce the critical ISS 610-Stat3 interactions. Hence, S3I-M2001 (FIG. 1B), which contained a central oxazole core with two hydrophobic substituents to complement the relatively hydrophobic protein surface and a pTyr group to bind to the phosphate recognition residues of the third pocket, and which superimposes well with the parent ISS 610 docked into the same SH2 cavity (FIG. 1A). Docking studies of S3I-M2001 identified significant complementary interactions between the protein surface and the molecule. The pTyr moiety is bound tightly within a hydrophilic cleft composed of Arg609, Ser613 and Ser611. This important contact may predetermine the subsequent orientations of the two lipophilic groups within the hydrophobic regions of the SH2 domain. The naphthyl appendage makes significant contact with the Ile634 side chain and the lipophilic hexyl substituent is partially encased within a hydrophobic channel composed primarily of Phe716 and Trp623. Positive cooperativity may exist between these subunits to provide a highly potent binding agent for the SH2 active site.

Stat3-Inhibitory Property of S3I-M2001.

Per DNA-binding assay/EMSA analysis (see "Methods" for details). S3I-M2001 favorably disrupts Stat3 activity in vitro in nuclear extracts containing activated Stat3 (FIG. 2A, left panel) or in lysates from Sf-9 cells containing activated Stat3, and preferentially inhibits Stat3 activity over Stat1 by 2-fold (IC50 values (mM), Stat3:Stat3, 79±09; Stat1:Stat3, 92±11; and Stat1:Stat1, 159±06 (FIG. 2A, middle and right panels). Similarly, per DNA-binding assay/EMSA analysis (FIG. 2B). SDS-PAGE/Western blot (FIG. 2C) and immunocytostaining analyses, S3I-M2001 inhibited constitutive Stat3 Tyr phosphorylation and activation in the NIH3T3/v-Src and the human breast cancer MDA-MB-231 and MDA-MB-435 cell lines that harbor constitutively-active Stat3 (16-18) (FIG. 2B, lanes 1-13, and 2C, lanes 1-6), and preferentially inhibited the epidermal growth factor (rhEGF)- induced Stat3 activation over that of Stat1 in the mouse fibroblasts overexpressing the human EGF receptor (NIH3T3/hEGFR) (FIG. 2B, right panel). Supershift analysis with anti-Stat3 antibody shows protein:DNA probe complex contains Stat3 (FIG. 2B, left panel, lane 8). By contrast, the pJak1, pSrc and pErk1/2 (MAPKs) in NIH3T3/v-Src fibroblasts are not repressed by S3I-M2001 (FIG. 2C, lanes 7-12), indicating minimal effect on non-Stat3-related proteins. Furthermore, transient transfection and luciferase reporter studies showed S3I-M2001 inhibited v-Src-induced Stat3-dependent pLucTKS3 luciferase reporter, but not the v-Src-induced Stat3-independent pLucSRE luciferase reporter (17, 19), in a similar manner to the effect of the transient co-expression of the dominant-negative Stat3b (FIG. 3A) (17, 19).

To confirm the disruption of Stat3:Stat3 dimerization, the previously reported dissociation-reassociation analysis (9, 10, 20) was performed using pooled cell lysates of independently-prepared lysates of activated Stat1 and Stat3 (details are provided in Supplementary Material, "RESULTS"). Stat1 or Stat3 DNA-binding activity was evident in their respective cell lysates (FIG. 3B, lanes 1 and 2) and present together in the pooled lysates (FIG. 3B, lane 3). Pooled lysate treated with S3I-M2001 showed a concentration-dependent diminution of Stat3:Stat3 DNA-binding activity (FIG. 3B, lanes 3-6) ahead of a diminishing Stat1:Stat1 homodimer activity (FIG. 3B, lanes 5-7), and the appearance of an intermediate band corresponding to Stat1:Stat3 heterodimer activity, which was hitherto not present (FIG. 3B, lanes 5 and 6). The formation of the Stat1:Stat3 band is due to the re-association between transient monomers of active Stat3 and Stat1 (9, 10). The disappearance of the activities for Stat3:Stat3 (FIG. 3B, lanes 5-7) and Stat1:Stat3 (FIG. 3B, lane 7) is due to dimer disruption, as previously observed for ISS 610 (9, 10), and suggests a preferential disruption of Stat3:Stat3 over Stat1:Stat1 homodimer (FIG. 2A, middle and right panels). By contrast, in vitro ELISA study of the pTyr-SH2 domain interaction between the unrelated Lck SH2-GST and its cognate phosphopeptide, biotinyl-e-Ac-EPQpYEEIEL-OH (22) (FIG. 3C, 4th bar) showed minimal effect of S3I-M2001 at 30 or 100 mM (FIG. 3C, compare bars 5 and 6 to bar 4). Thus, S3I-M2001 selectively disrupts Stat3:Stat3 dimers, thereby inhibiting Stat3 DNA-binding and transcriptional activities, while not affecting the Lck-SH2 domain function. On whether disruption of Stat3 dimerization inhibits nuclear translocation, immunofluorescence imaging/confocal microscopy for the nuclear localization of Stat3 in EGF-stimulated NIH3T3/hEGFR mouse fibroblasts revealed a strong EGF-induced nuclear staining of Stat3 in the absence of S3I-M2001 (FIG. 3D, 3rd panel from left), which was significantly attenuated upon treatment of cells with S3I-M2001 (FIG. 3D, 4th panel from left), suggesting inhibition of Stat3 activation blocks its nuclear localization.

Intracellular Stat3 Processing.

Malignant cell requirement for persistently-active Stat3 for the maintenance of the malignant phenotype is well-established (17-19, 32, 33). How tumor cells regulate Stat3 to meet this requirement, however, is not defined. Moreover, while the inhibition of aberrant Stat3 activity results in malignant cells demise (9-13), the molecular details of Stat3 cellular processing and the fate of the protein within the context of such an inhibition have not been explored. Given S3I-M2001's specific anti-Stat3 properties, it was used to probe the intracellular processing and localization dynamics of aberrant Stat3. Fluorescent microscopy (Nikon Eclipse TE200) (FIG. 4A) and laser scanning confocal microscopy (FIG. 4B-4E) of the NIH3T3/v-Src fibroblasts stably-transfected with the yellow fluorescent protein (YFP)-tagged Stat3 (Stat3-YFP) plasmid (23) (NIH3T3/v-Src/Stat3-YFP) showed a stronger nuclear Stat3-YFP signal, consistent with constitutive Stat3 activation (FIGS. 4A, 4B and 4D, right panel, and 4E). Treatment with S3I-M2001 induced a time-dependent decrease in the Stat3-YFP fluorescence; there is no change in signal at 1 h-treatment or less, while an increasing degree of Stat3 fluorescence loss becomes evident from 2-5 h, 100-300 mM S3I-M2001-treatment (FIG. 4A, time t=0 to t=6 h, left panels; arrows denote Stat3-YFP signal; FIG. 4B, second column from left compared to first, time t=0 to t=2 h: FIG. 4D, right panel, time t=0 to t=5 h)). Phase contrast microscopy showed cellular integrity was maintained (FIG. 4A, time t=0 to t=6 h, right panels; arrows identify cells remaining or originally positive for fluorescent signal). Protein degradation can result in fluorescence signal loss (29). Accordingly, the presence of MG132 proteasome inhibitor prevented the fluorescence loss (FIG. 4B, third column from left), while MG132 alone has no appreciable effect (FIG. 4B, fourth column from left), suggesting the Stat3 fluorescence decay may involve the ubiquitin-proteasome degradation pathway. In contrast, similar studies with the v-Src transformed fibroblasts stably expressing the non-Stat3 related Green Fluorescent Protein (GFP) (NIH3T3v-Src/GFP) showed no evidence of GFP signal change by S3I-M2001 or the proteasome inhibitor MG132 (FIG. 4C and FIG. 4D, left panel), thus excluding the possibility of non-specific fluorescence quenching or photobleaching. Moreover, immunoblotting of whole-cell lysates from NIH3T3/v-Src/Stat3-YFP fibroblasts showed reduced Stat3-YFP expression in S3I-M2001-treated cells in 3 and 5 h, which was similarly partially restored when cells were co-treated with MG132 (FIG. 5A, lanes 3 and 4 vs. lanes 5 and 6). That only a partial corresponding decrease in total Stat3 protein occurred (FIG. 5A, middle panel, lanes 3 and 4) suggests a weak proteasome activity against total Stat3 protein. However, immunoblotting for ubiquitin of Stat3 immunoprecipitates (i.p.) from NIH3T3/v-Src fibroblasts showed a strong and time-dependent increase in the level of Stat3 ubiquitination following the S3I-M2001 treatment, which occurred in parallel with partial and strong Stat3 protein reductions at 5 and 24 h, respectively (FIG. 5B). These findings together raise the possibility there is an impairment of proteasome function (24, 25) at the early hours (<5 h) of S3I-M2001-treatment and suggests additional mechanisms contribute to the Stat3 fluorescence signal decay.

Protein misfolding can lead to ubiquitin-proteasome degradation, and aggregation into aggresomes (26-29). Aggresomes can lead to fluorescence signal loss (29) and impairment of proteasome function (24, 25). Using laser scanning confocal microscopy, we observed that the specific loss of Stat3-YFP signal in the NIH3T3/v-Src/Stat3-YFP that follows S3I-M2001-treatment (FIG. 4D, right column and 4E right column, time t=0 to t=5 h) is accompanied by aggregated bodies, possibly aggresomes of Stat3-YFP, within 5 h of S3I-M2001 treatment (FIG. 4E, right bottom panel; red arrow denotes bodies). By contrast, Cisplatin treatment produced no such effect (FIG. 4E middle column). Confirming these data, immunofluorescence imaging/confocal microscopy of Stat3 in NIH3T3/v-Src fibroblasts revealed that in contrast to the strong nuclear fluorescence of activated Stat3 protein that occurred in "dot-like" structures resembling nuclear bodies (23) and the low cytoplasmic signal in the untreated cells (FIG. 6A, control), a strongly reduced Stat3 fluorescence signal occurred that coincided with the appearance of perinuclear aggregated bodies, possibly aggresomes in the S3I-M2001-treated cells within 3 h and later, with a stronger aggresome formation at 24-h treatment (FIG. 6A. S3I-M2001, time t=0.5 to t=24 h). Thus. S3I-M2001 promotes the disruption of activated Stat3 from "dot-like" nuclear bodies (23) into perinuclear aggresomes, which may explain the apparent low proteasome-mediated degradation in the early period of S3I-M2001-treatment. The Stat3 aggresome formation and signal loss are events specific to S3I-M2001, because they are not induced by Cisplatin (FIG. 6A, Cisplatin) and occur in the early hours (<5 h) of treatment prior to change in cellular integrity (FIG. 4A and data not shown). The resting of NIH3T3/v-Src fibroblasts for 2 h following a 5-h S3I-M2001-treatment led to a partial recovery of Stat3 signal, while aggresomes remained (FIG. 6B, upper panel, compare right column vs. middle column, 5 h-treated cells without recovery vs. control), suggesting effect of S3I-M2001 still persisted in the 2 h following drug removal. By contrast, Stat3 immunofluorescence was completely recovered within 19-h of resting after 5-h treatment (FIG. 6B, lower panel, compare right column vs. middle column, 5 h-treated cells without recovery vs. control), either because S3I-M2001's effect on Stat3 was reversible or that new Stat3 protein was synthesized. To investigate further and to demonstrate the perinuclear aggresome localization, immunofluorescence imaging/confocal microscopy was performed on NIH3T3/v-Src fibroblasts harboring constitutively-active Stat3 to assess the colocalization with Hook2, an adaptor protein important for the association of cargos with dynein for the transport on microtubules and for aggresome formation (26). As expected, a strong nuclear Stat3 staining is observed (FIG. 6C, left upper panel), which contrasts a Hook2 expression that appears ubiquitous (FIG. 6C, middle upper panel), without any evidence of colocalization. By contrast, S3I-M2001 induced the formation of perinuclear aggregated bodies of Stat3 (FIG. 6C, left bottom panel), which colocalized with Hook2 (FIG. 6C, middle and right bottom panels; red arrows denote aggregated bodies), suggesting a possible association between the two proteins and implicating the Hook proteins in the Stat3 aggresome formation.

Together, our studies herein disclosed are the first on the localization dynamics and the molecular mechanisms for terminating Stat3 function in response to a small-molecule inhibitor. Two possible mechanisms may account for the loss of aberrant Stat3 function: one involves protein ubiquitination and an early aggregation into perinuclear aggresomes (28), and a late-phase proteasome-mediated degradation event, potentially a "quality control" mechanism for Stat3 (34), given its apparent unnatural state promoted by S3I-M2001. The effects of early aggresome formation may be reversible, while the late-phase events are irreversible and lead to a long-term loss of Stat3 function, with biological consequences. The perinuclear aggresome formation also suggests a nuclear-to-perinuclear exit of disrupted "activated" Stat3 by as yet undetermined mechanisms.

Suppression of Malignant Phenotype and Tumor Growth.

Consistent with Stat3's importance in maintaining the malignant phenotype (17), WST-1 assay (FIG. 7A) and trypan blue exclusion/cell counting revealed S3I-M2001-induced growth inhibition and a greater than 2-fold selective loss of viability of the human breast (MDA-MB-435 and MDA-MB-231) and Pancreatic (Panc-1) cancer cells, and the NIH3T3/v-Src fibroblasts, which all harbor constitutively-active Stat3, with EC50 values in the range of 50-100 mM, compared to effects on normal NIH3T3 fibroblasts, and the human breast (MDA-MB-453) and Pancreatic (MiaPaca-1) cancer cells that lack aberrant Stat3 (EC50 values of 120-300 mM) (FIG. 7A). Furthermore, S3I-M2001 blocked growth in soft-agar of the NIH3T3/v-Src and the pancreatic cancer, Panc-1 cells (FIG. 7B), and induced morphology changes in NIH3T3/v-Src, in contrast to no appreciable effects on v-Ras transformed fibroblasts (NIH3T3/v-Ras) lacking constitutively-active Stat3 (FIG. 7B). Terminal nucleotidyl transferase-mediated nick end labeling (TUNEL) (FIG. 7C) and Annexin V binding with Flow Cytometric Analyses (FIG. 7D, first and third pairs of bars) showed strong apoptosis in the NIH3T3/v-Src (3T3/v-Src) and MDA-MB-231 and MDA-MB-435 cells harboring aberrant Stat3 and treated with S3I-M2001, compared to minimal effect on normal NIH3T3, human breast epithelial MCF-10A, breast cancer MDA-MB-453, and HUVEC, HAEC, and HL-60 cells that do not contain aberrant Stat3. Validating that the S3I-M2001-induced apoptosis is due to interaction with its molecular target (Stat3 SH2 domain), NIH3T3/v-Src fibroblasts (3T3/v-Src) transiently-transfected with a plasmid encoding the Stat3 SH2 domain (3T3/v-Src/ST3-SH2) and treated with S3I-M2001 showed diminished apoptosis (FIG. 7D, compare middle two bars) compared to mock-transfected (3T3/v-Src/pcDNA3) (FIG. 7D, left two bars) or untransfected cells (FIG. 7D, right two bars). Moreover, Western blot analysis showed diminished Bcl-xL expression, a known Stat3-regulated and antiapoptotic gene (30), in the S3I-M2001-treated NIH3T3/v-Src and MDA-MB-435 cells (FIG. 7E), suggesting repressed Bcl-xL expression is part of the underlying mechanism for the S3I-M2001-induced apoptosis.

Given Stat3's importance in tumor growth and tumor progression (31), matrigel assay using Bio-Coat migration chambers showed significant S3I-M2001-induced inhibition of the migration of NIH3T3/v-Src (76%). MDA-MB-231 (37%) and Panc-1 (21%), and the invasion of NIH3T3/v-Src (28%), MDA-MB-231 (48%) and Panc-1 (38%) cells harboring constitutively-active (FIG. 8A: percent inhibition in parenthesis defined in "Methods" section). Furthermore, in xenograft models of human breast (MDA-MB-231 cells that harbors aberrant Stat3) tumor-bearing mice, the i.v. injection of S3I-M2001 at 5, 10, and 20 mg kg-1, but not vehicle (control) every 2 or 3 days for 26 days, strongly inhibited growth of tumors (FIG. 8B). Animals remained viable at the highest (20 mg kg-1) dose applied. DNA-binding assay with EMSA analysis and SDS/AGE-Western blotting of lysates from residual tumor tissues extracted from representative control and treated mice showed abrogated Stat3 activity and pTyr levels in S3I-M2001-treated tumors (T1 and T2) (FIGS. 8C and 8D). These findings together demonstrate S3I-M2001 induces antitumor cell effects and tumor regression in part by targeting the Stat3 SH2 domain and inhibiting Stat3-mediated tumor processes (3, 6, 7, 17, 32, 38, 39). Moreover, S3I-M2001 compares favorably with other Stat3 SH2 domain-targeting small-molecule inhibitors, including S3I-201, which was obtained by computational modeling and virtual chemical library-screening (13), and represents a significant improvement over its peptidomimetic predecessors (10).

The present disclosure provides the first study of the cellular processing and stability of aberrant Stat3 in malignant cells within the context of inhibition by a chemical probe that has implications for the many human tumor cells, including the human breast and pancreatic cancer cells that harbor aberrant Stat3. The general applicability of the current study to other previously-identified Stat3 inhibitors, including the g-quartet oligonucleotides (35), peptide aptamers (36), platinum (IV) complexes (11, 12), and STA-21 (NSC 628869) (37), however, is unclear, as those other agents have different modes of inhibition of Stat3 from S3I-M2001. Altogether, our studies establish the proof-of-concept for the antitumor effects of S3I-M2001 that correlates with disruption of constitutively-active Stat3:Stat3 dimers, while using S3I-M2001 as a chemical probe to investigate the molecule dynamics of termination of Stat3 function following inhibition. Accordingly, the novel compound S3I-M2001 herein disclosed may also be referred to as an anti-cancer agent, a cytotoxic agent and/or a chemotherapeutic agent.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES

1. Darnell, J. E., Jr. (1996) The JAK-STAT pathway: summary of initial studies and recent advances. Recent Prog. Norm. Res. 51, 391-403.
2. Darnell, J. E., Jr. (1997) STATs and gene regulation. Science 277, 1630-1635.
3. Darnell. J. E. Validating Stat3 in cancer therapy (2005) Nat. Med. 11, 595-596.
4. Bowman, T., Garcia, R., Turkson. J., and Jove, R. (2000) STATs in oncogenesis. Oncogene 19, 2474-2488.
5. Buettner, R., Mora, L. B., and Jove, R. (2002) Activated STAT signaling in human tumors provides novel molecular targets for therapeutic intervention. Clin. Cancer Res. 8, 945-954.
6. Yu, H. and Jove. R. (2004) The STATS of Cancer-New molecular targets come of age. Nat. Rev. Cancer 4, 97-105.
7. Turkson, J. (2004) STAT proteins as novel targets for cancer drug discovery. Expert Opin. Ther. Targets 8.409-422.
8. Haura, E. B., Turkson, J., and Jove, R. (2005) Mechanisms of disease: Insights into the emerging role of signal transducers and activators of transcription in cancer. Nat. Clin. Pract. Oncol. 2, 315-324.
9. Turkson. J. Ryan, D., Kim. J. S., Zhang, Y., Chen, Z., Haura, E., Laudano, A., Sebti, S., Hamilton, A. D., and Jove, R. (2001) Phosphotyrosyl peptides block Stat3-mediated DNA-binding activity, gene regulation and cell transformation. J. Biol. Chem. 276, 45443-45455.
10. Turkson, J. Kim. J. S., Zhang. S., Yuan, J., Huang. M., Glenn, M., Haura, E., Sebti, S. Hamilton. A. D., and Jove, R. (2004) Novel peptidomimetic inhibitors of signal transducer and activator of transcription 3 dimerization and biological activity. Mol. Cancer Ther. 3, 261-269.
11. Turkson. J., Zhang, S. Palmer, J., Kay, H., Stanko, J., Mora, L. B., Sebti, S., Yu, H., and Jove, R. (2004) Inhibition of constitutive signal transducer and activator of transcription 3 activation by novel platinum complexes with potent anti-tumor activity. Mol. Cancer. Ther. 3, 1533-1542.
12. Turkson, J., Zhang, S., Mora, L. B., Burns, A., Sebti, S., and Jove, R. (2005) A novel platinum compound inhibits constitutive Stat3 signaling and induces cell cycle arrest and apoptosis of malignant cells. J. Biol. Chem. 280, 32979-32988.
13. Siddiquee, K., Zhang, S., Guida. W. C., Blaskovich, M. A. Greedy, B., Lawrence, H. R., Yip, M. L., Jove. R., McLaughlin. M. M., Lawrence, N. J., Sebti, S. M., and Turkson, J. (2007) Selective chemical probe inhibitor of Stat3, identified through structure-based virtual screening, induces antitumor activity. Proc. Natl. Acad. Sci. USA. 104, 7391-7396.
14. Becker, S., Groner, B., and Muller. C. W. (1998) Three-dimensional structure of the Stat3beta homodimer bound to DNA. Nature 394, 145-151.
15. Jones, G., Willett, P., Glen, R. C., Leach, A. R., and Taylor, R. (1997) Development and validation of a genetic algorithm for flexible docking. J. Mol. Biol. 267, 727-748.
16. Yu, C. L., Meyer, D. J., Campbell, G. S., Lamer, A. C., Carter-Su, C., Schwartz, J., and Jove. R. (1995) Enhanced DNA-binding activity of a Stat3-related protein in cells transformed by the Src oncoprotein. Science 269, 81-83.
17. Turkson, J., Bowman, T., Garcia, R., Caldenhoven, E., De Groot, R. P., and Jove, R. (1998) Stat3 activation by Src induces specific gene regulation and is required for cell transformation. Mol. Cell. Biol. 18, 2545-2552.
18. Garcia, R., Bowman. T. L., Niu, G., Yu, H., Minton, S., Muro-Cacho. C. A. Cox. C. E., Falcone, R., Fairclough. R., Parson, S., Laudano, A., Gazit. A., Levitzki, A. Kraker, A., and Jove, R. (2001) Constitutive activation of Stat3 by the Src and JAK tyrosine kinases participates in growth regulation of human breast carcinoma cells. Oncogene 20, 2499-2513.
19. Turkson. J., Bowman, T., Adnane, J., Zhang, Y., Djeu. J. Y., Sekharam. M., Frank, D. A., Holzman, L. B., Wu, J., Sebti, S., and Jove, R. (1999) Requirement for Ras/Rac1-Mediated p38 and c-Jun N-Terminal Kinase Signaling in Stat3 Transcriptional Activity Induced by the Src Oncoprotein. Mol. Cell. Biol. 19, 7519-7528.
20. Shuai, K., Horvath. C. M., Huang. L. H., Qureshi, S. A., Cowburn, D., and Darnell, J. E., Jr. (1994) Interferon activation of the transcription factor Stat91 involves dimerization through SH2-phosphotyrosyl peptide interactions. Cell 76, 821-828.
21. Zhang, Y., Turkson, J., Carter-Su, C., Smithgall, T., Levitzki, A. Kraker, A., Krolewski, J. J., Medveczky, P., and Jove, R. (2000) Activation of Stat3 in v-Src Transformed Fibroblasts Requires Cooperation of Jak1 Kinase Activity. J. Biol. Chem. 275, 24935-24944.
22. Lee, T. R. and Lawrence, D. S. (2000) SH2-directed ligands of the Lck tyrosine kinase. J. Med. Chem. 43, 1173-1179.
23. Herrmann, A., Sommer, U., Pranada, A. L., Giese. B., Kuster. A., Haan, S., Becker, W., Heinrich, P. C., and Muller-Newen, G. (2004) STAT3 is enriched in nuclear bodies. J. Cell Sci. 117, 339-349.
24. Bence, N. F., Sampat, R. M., and Kopito, R. R. (2001) Impairment of the ubiquitin-proteasome system by protein aggregation. Science. 29, 1552-1555.
25. Bennett, E. J., Bence, N. F., Jayakumar, R., and Kopito, R. R. (2005) Global impairment of the ubiquitin-proteasome system by nuclear or cytoplasmic protein aggregates precedes inclusion body formation. Mol. Cell. 17.351-365.
26. Szebenyi, G., Wigley, W. C., Hall, B., Didier, A., Yu, M., Thomas, P., and Kramer. H. (2007) Hook2 contributes to aggresome formation. BMC Cell Biology 8, 19.
27. Johnston. J. A., Ward, C. L., and Kopito, R. R. (1998) Aggresomes: a cellular response to misfolded proteins. J. Cell. Biol. 143, 1883-1898.
28. Garcia-Mata, R., Bebok, Z., Sorscher, E. J., and Sztul, E. S. (1999) Characterization and dynamics of aggresome formation by a cytosolic GFP-chimera. J. Cell. Biol. 146, 1239-1254.
29. Gelman, M. S., Kannegaard, E. S., and Kopito, R. R. (2002) A principal role for the proteasome in endoplasmic reticulum-associated degradation of misfolded intracellular cystic fibrosis transmembrane conductance regulator. J. Biol. Chem. 277, 11709-11714.
30. Catlett-Falcone, R., Landowski, T. H., Oshiro, M. M., Turkson, J., Levitzki, A., Savino, R., Gilberto. G., Moscinski, L., Femandez-Luna, J. L. Nuñez. G. Dalton, W. S., and Jove, R. (1999) Constitutive activation of Stat3 signaling confers resistance to apoptosis in human U266 myeloma cells. Immunity 10, 105-115.
31. Huang, C., Cao, J., Huang, K. J. Zhang, F., Jiang, T., Zhu, L., and Qiu, Z. J. (2006) Inhibition of STAT3 activity with AG490 decreases the invasion of human pancreatic cancer cells in vitro. Cancer Sci. 97, 1417-1423.

32. Bromberg, J. F., Horvath. C. M., Besser, D., Lathem, W. W., and Darnell. J. E., Jr. (1998) Stat3 activation is required for cellular transformation by v-src. *Mol. Cell. Biol.* 18, 2553-2558.
33. Nam, S., Buettner, R., Turkson, J., Kim, D., Cheng. J. Q., Muehlbeyer, S., Hippe, F., Vatter, S., Merz. K. H., Eisenbrand, G., and Jove, R. (2005) Indirubin derivatives inhibit Stat3 signaling and induce apoptosis in human cancer cells. *Proc. Natl. Acad. Sci. USA.* 102, 5998-6003.
34. Ciechanover, A., Orian, A., and Schwartz, A. L. (2000) Ubiquitin-mediated proteolysis: biological regulation via destruction. *Bioessays* 22, 442-451.
35. Jing, N., Li, Y., Xu, X., Sha. W., Li, P., Feng, L., and Tweardy, D. J. (2003) Targeting Stat3 with G-quartet oligodeoxynucleotides in human cancer cells. *DNA Cell Biol.* 22, 685-696.
36. Nagel-Wolfrum, K. Buerger, C., Wittig, I., Butz, K. Hoppe-Seyler, F., and Groner, B. (2004) The interaction of specific peptide aptamers with the DNA binding domain and the dimerization domain of the transcription factor Stat3 inhibits transactivation and induces apoptosis in tumor cells. *Mol. Cancer. Res.* 2, 170-182.
37. Song. H., Wang, R. Wang. S., and Lin, J. (2005) A low-molecular-weight compound discovered through virtual database screening inhibits Stat3 function in breast cancer cells. *Proc. Natl. Acad. Sci. USA.* 102, 4700-4705.
38. Turkson, J. and Jove, R. (2000) STAT proteins: novel molecular targets for cancer drug discovery. *Oncogene* 19, 6613-6626.
39. Scholz, A., Heinze, S., Detjen, K. M., Peters, M., Welzel, M., Hauff. P., Schirner, M., Wiedenmann, B., and Rosewicz, S. (2003) Activated signal transducer and activator of transcription 3 (STAT3) supports the malignant phenotype of human pancreatic cancer. *Gastroenterology* 125, 891-905.
40. Garcia, R., Yu. C. L., Hudnall, A., Catlett, R., Nelson, K. L. Smithgall, T., Fujita, D. J., Ethier, S. P., and Jove, R. (1997) Constitutive activation of Stat3 in fibroblasts transformed by diverse oncoproteins and in breast carcinoma cells. *Cell Growth Diff.* 8, 1267-1276.
41. Wipf, P. and Miller, C. P. (1993) Stereospecific synthesis of peptide analogs with allo-threonine and D-allo-threonine residues. *J. Org. Chem.* 58. 3604-3606.
42. Wagner, B. J., Hayes. T. E., Hoban, C. J., and Cochran, B. H. (1990) The SIF binding element confers sis/PDGF inducibility onto the c-fos promoter. *EMBO J.* 9, 4477-4484.

That which is claimed:

1. A compound, or a pharmaceutically acceptable salt thereof, having a structure represented by a formula:

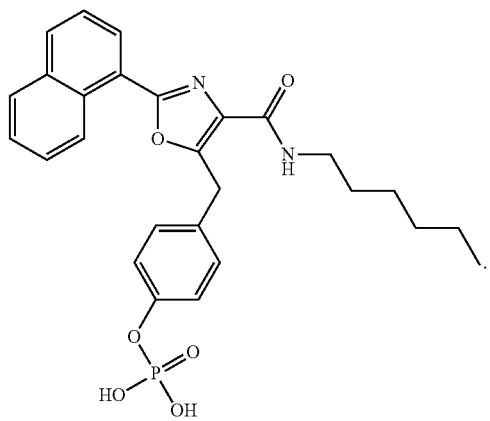 [SMILES: CCCCCCNC(=O)c1nc(-c2cccc3ccccc23)oc1Cc1ccc(OP(=O)(O)O)cc1]

2. A pharmaceutically acceptable composition containing the compound of claim 1.

3. A pharmaceutically acceptable composition containing the compound of claim 1 in an effective amount for inhibiting Stat3 dimerization in a mammalian cell contacted with said composition.

4. A method of treating a mammalian cell having a dysfunctional Stat3 protein, the method comprising contacting the cell with the compound of claim 1.

5. A method of treating a mammalian cell, the method comprising contacting the cell with the composition of claim 2.

6. A method of treating a mammalian cell having a dysfunctional Stat3 protein, the method comprising contacting the cell with the composition of claim 2.

7. A method of inhibiting a mammalian cell harboring constitutively active Stat3, the method comprising contacting the cell with an effective amount of the compound of claim 1.

8. A method of treating a human breast cancer cell or pancreatic cancer cell, the method comprising contacting the cell with an effective amount of the compound of claim 1 to inhibit Stat3 activity therein.

9. A method of treating human breast or pancreatic cancer cells having a constitutively active level of Stat3, the method comprising administering a sufficient amount of the compound of claim 1 to contact said cancer cells.

10. A method of treatment effective to inhibit growth of a human breast cancer tumor cell, the method comprising administering to the cell a sufficient amount of the compound of claim 1.

11. A method of inhibiting migration of a malignant cell, the method comprising contacting the cell with the compound of claim 1.

12. A method of treating a mammalian cancer having a dysfunctional level of Stat3, the method comprising contacting the cancer with a therapeutically effective amount of the compound having a structure represented by a formula:

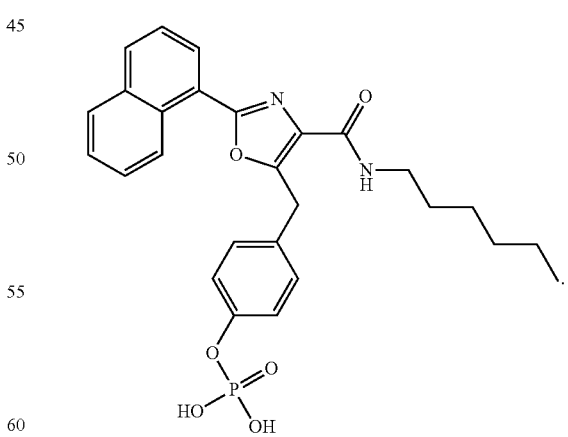

13. A method of treating a mammalian cancer having a dysfunctional Stat3 protein, the method comprising contacting the cancer with the compound having a structure represented by a formula:

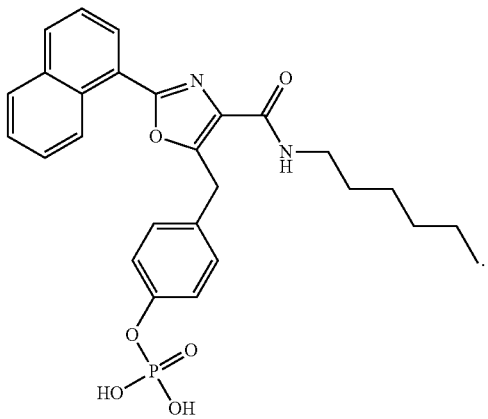 [SMILES: CCCCCCNC(=O)c1nc(-c2cccc3ccccc23)oc1Cc1ccc(OP(=O)(O)O)cc1]

14. A method of treating a human breast or pancreatic cancer cell, the method comprising contacting at least one cell of a human breast or pancreatic cancer with the composition of claim 2.

15. A method of treating a mammalian cancer having a dysfunctional Stat3 protein, the method comprising contacting the cell with the composition of claim 2.

16. A method of inhibiting a mammalian cancer having a constitutively active Stat3, the method comprising contacting the cancer with an effective amount of the compound of claim 1.

17. A method of treating a human breast cancer or pancreatic cancer, the method comprising contacting the cancer with an amount of the compound of claim 1 effective to inhibit Stat3 activity therein.

18. A method of treating human breast or pancreatic cancer having a constitutively active level of Stat3, the method comprising administering a sufficient amount of the compound of claim 1 to contact said cancer.

19. A method of patient treatment effective for inhibiting growth of a human breast cancer tumor, the method comprising administering to the patient a sufficient amount of the compound of claim 1 to contact the cancer tumor.

20. A method of inhibiting migration of malignant cells from a mammalian cancer, the method comprising contacting the cells with the compound of claim 1.

21. A method of inhibiting growth of a human breast or pancreatic cancer tumor, the method comprising contacting at least one cell of a human breast or pancreatic cancer tumor with the compound of claim 1.

* * * * *

UNITED STATES PATENT AND TRADEMARK OFFICE
CERTIFICATE OF CORRECTION

PATENT NO. : 8,609,639 B2  Page 1 of 1
APPLICATION NO. : 12/517453
DATED : December 17, 2013
INVENTOR(S) : Turkson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1183 days.

Signed and Sealed this
Twenty-second Day of September, 2015

Michelle K. Lee
*Director of the United States Patent and Trademark Office*